United States Patent
Fujimaki et al.

(10) Patent No.: US 7,394,082 B2
(45) Date of Patent: Jul. 1, 2008

(54) ION BEAM DELIVERY EQUIPMENT AND AN ION BEAM DELIVERY METHOD

(75) Inventors: Hisataka Fujimaki, Hitachinaka (JP); Koji Matsuda, Hitachi (JP); Hiroshi Akiyama, Hitachiohta (JP); Masaki Yanagisawa, Hitachi (JP); Alfred R. Smith, Houston, TX (US); Kazuo Hiramoto, Hitachiohta (JP)

(73) Assignees: Hitachi, Ltd., Tokyo (JP); Board of Regents, The University of Texas System, Austin, TX (US)

( * ) Notice: Subject to any disclaimer, the term of this patent is extended or adjusted under 35 U.S.C. 154(b) by 224 days.

(21) Appl. No.: 11/414,204

(22) Filed: May 1, 2006

(65) Prior Publication Data
US 2007/0252093 A1 Nov. 1, 2007

(51) Int. Cl.
*A61N 5/00* (2006.01)
(52) U.S. Cl. .................. 250/492.3; 250/398; 250/397; 250/396 R
(58) Field of Classification Search .............. 250/492.3, 250/398, 397, 396 R, 505.1
See application file for complete search history.

(56) References Cited
U.S. PATENT DOCUMENTS
5,363,008 A 11/1994 Hiramoto et al.

2004/0200983 A1 * 10/2004 Fujimaki et al. ......... 250/492.3
2006/0273264 A1 * 12/2006 Nakayama et al. ....... 250/492.3

FOREIGN PATENT DOCUMENTS
EP 1020204 A1 * 7/2000

OTHER PUBLICATIONS

Review of Scientific Instruments, vol. 64, No. 8, pp. 2074-2084.
"Monitor unit calculations for range-modulated spread-out Bragg peak fields" by H. Kooy, et al. Physics in Medicine and Biology 48 (2003) 2797-2808.

* cited by examiner

Primary Examiner—Jack I. Berman
Assistant Examiner—Michael Maskell
(74) Attorney, Agent, or Firm—Mattingly, Stanger, Malur & Brundidge, P.C.

(57) ABSTRACT

The invention is intended to confirm whether the SOBP (spread-out Bragg peak) width is a desired value in real time during beam irradiation, and to improve safety in treatment. Ion beam delivery equipment comprises a beam generator including a synchrotron, an RMW (range modulation wheel) device for forming an SOBP width of an ion beam extracted from the beam generator, a beam delivery nozzle including a reference dose monitor and a main dose monitor which are installed respectively upstream and downstream of the RMW device in the direction of travel of the ion beam, and an SOBP width computing unit for computing the SOBP width of the ion beam, which is formed by the RMW device, based on values detected by both the reference dose monitor and the main dose monitor.

31 Claims, 10 Drawing Sheets

ABSORBED DOSE DISTRIBUTION AT POSITION OF REFERENCE MONITOR
(ENERGY OF ION BEAM: LOW)

ABSORBED DOSE DISTRIBUTION AT POSITION OF MAIN DOSE MONITOR
(ENERGY OF ION BEAM: LOW)

FIG. 16

| IRRADIATION FIELD SIZE | RANGE | BEAM Eg | SC1 THICK-NESS | SOBP WIDTH | SC2 TYPE | RS THICK-NESS | BC APER-TURE SIZE |
|---|---|---|---|---|---|---|---|
| φ20[cm] | 40[mm] ⋮ 90[mm] | 100[MeV] | 2[mm] | 1-1 | 1-1 | 50[mm] ⋮ 0[mm] | φ20[cm] |
| | 90[mm] ⋮ 150[mm] | 150[MeV] | 4[mm] | 1-2 | | 60[mm] ⋮ 0[mm] | |
| | 150[mm] ⋮ | 200[MeV] | 7[mm] | 1-3 | 1-2 | ⋮ 0[mm] | |
| | ⋮ | 250[MeV] | 10[mm] | 1-4 | | ⋮ 0[mm] | |
| φ6[cm] | 40[mm] ⋮ 90[mm] | 100[MeV] | 1[mm] | 2-1 | 2-1 | 50[mm] ⋮ 0[mm] | φ6[cm] |
| | 90[mm] ⋮ 150[mm] | 150[MeV] | 2[mm] | 2-2 | | 60[mm] ⋮ 0[mm] | |
| | 150[mm] ⋮ | 200[MeV] | 3.5[mm] | 2-3 | 2-2 | ⋮ 0[mm] | |
| | ⋮ | 250[MeV] | 5[mm] | 2-4 | | ⋮ 0[mm] | |

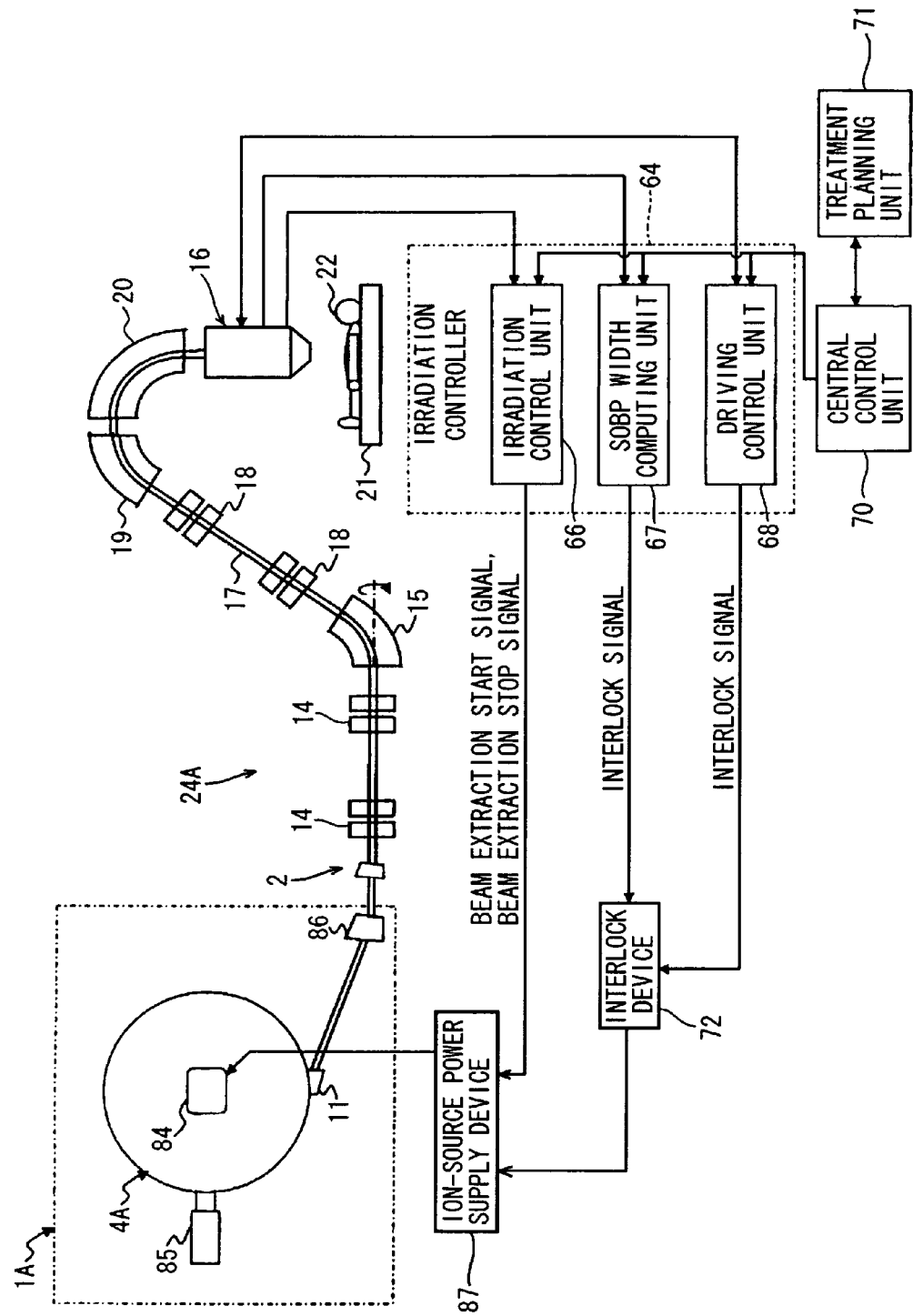

ION BEAM DELIVERY EQUIPMENT AND AN ION BEAM DELIVERY METHOD

BACKGROUND OF THE INVENTION

1. Field of the Invention

The present invention relates to an ion beam delivery equipment and an ion beam delivery method, which are used to produce and deliver ion beam of, e.g., proton or carbon ions to a tumor for treatment.

2. Description of the Related Art

There is known a treatment method for delivering ion beam, e.g., proton or carbon ions, to a tumor, such as a cancer, in the body of a patient. The ion beam delivery equipment for such treatment is comprised of a beam generator to produce the ion beam and accelerate it to a needed energy, a beam transport system, and a beam delivery nozzle. An ion beam accelerated by the beam generator reaches the beam delivery nozzle, which is installed in a rotating gantry to monitor and shape the therapeutic radiation field, through a first beam transport system and a second beam transport system, the latter being installed in the rotating gantry. The ion beam reaching the beam delivery nozzle is delivered to the tumor in the patient's body from the beam delivery nozzle. Known examples of the beam generator include a synchrotron (quasi-circular accelerator) provided with an extraction deflector for extracting the ion beam from the orbit (see, e.g., Patent Reference 1; U.S. Pat. No. 5,363,008).

In radiation therapy using an ion beam, e.g., with a proton beam delivering a radiation dosage to the tumor, by utilizing characteristics that most of energy of the proton beam is released just before protons come to rest, namely that a Bragg peak is formed just before the protons stop. The energy of the proton beam is selected to stop protons in the tumor so that the beam energy is released mostly to cells within the tumor or its microscopic extensions.

Usually, the tumor has a certain thickness in the direction of depth, i.e. along the direction of the ion beam, from the body surface of a patient (hereinafter referred to simply as "the direction of depth"). To effectively irradiate the ion beam over the entire thickness of the tumor in the direction of depth, the width of the Bragg peak must be spread out in the direction of depth. To obtain the required spread-out Bragg peak width, the energy of the ion beam is changed, that is, modulated.

From that point of view, a range modulation wheel (RMW) has already been proposed in which a plurality of blades each having a thickness varied step by step in the circumferential direction are set around a rotating shaft (see, e.g., Non-patent Reference 1; "REVIEW OF SCIENTIFIC INSTRUMENTS", Vol. 64, No. 8, pp 2074-2084 and FIGS. 30 to 32, in particular, p 2077 and FIG. 30 (August 1993) and Non-patent Reference 2; "PHYSICS IN MEDICINE AND BIOLOGY", Vol. 48, No. 17, pp 2797-2808 (Sep. 7, 2003)). The plural blades are mounted to the rotating shaft. At the time when the ion beam passes through the blade, the energy of the ion beam is attenuated more as the ion beam passes through the blade having a larger thickness, and therefore the Bragg peak is produced in a portion of the tumor near the body surface of the patient. With the rotation of the RMW, the position in the direction of depth where the Bragg peak is formed varies cyclically. As a result, a Bragg peak width comparatively wide and flat in the direction of depth of the tumor can be obtained, looking at the beam energy integrated over time. Further, it is known that the SOBP (Spread-out Bragg Peak) width can also be formed by using a ridge filter (see, e.g., Non-patent Reference 1; in particular, p 2078 and FIG. 31).

The dose irradiated to the tumor can be determined through steps of detecting charge ionized in a dose monitor, and converting the detected value into a value of the actually absorbed dose by employing the conversion coefficient. The dose monitor is installed upstream of the patient along the beam path. Then, it is suggested that the coefficient for conversion between the detected value measured by the dose monitor and the value of the dose actually irradiated to the tumor is correlated to the beam penetration depth and the SOBP width (see, e.g., Non-patent Reference 2).

SUMMARY OF THE INVENTION

Some inventors of this application have previously invented and filed the ion beam delivery equipment for performing extraction-on/off control of an ion beam from a synchrotron during rotation of the RMW. With that preceding invention, by rotating the RMW such that the ion beam passes the RMW for a comparatively long time, i.e., over a wider range of RMW rotational angle, the attenuation of the ion beam is varied to a large extent, and hence the SOBP width is increased. On the other hand, by rotating the RMW such that the ion beam passes the RMW for a comparatively short time, i.e., over a narrower range of RMW rotational angle, the attenuation of the ion beam is varied to a small extent, and hence the SOBP width is decreased. Thus, the extraction-on/off control of the ion beam during the rotation of the RMW enables the SOBP width to be produced in various values by one RMW. It is therefore possible to reduce the frequency at which the RMW is to be replaced by another RMW, and to smoothly carry out the treatment for a larger number of patients.

Further studies conducted by the inventors of this application on the preceding invention, however, showed that the preceding invention had yet room for improvement in the point given below.

According to the preceding invention, the beam generating operation can be controlled for each patient, and the SOBP width can be obtained depending on the tumor size in the patient body. However, whether the SOBP width is the prescribed value corresponding to the tumor thickness in the patient body can be confirmed only by a method of totally absorbing the beam in material placed in the beam path and measuring the absorbed dose. In other words, a method for confirming whether the SOBP width is the needed value in real time during the beam irradiation is not yet established, and further improvement is demanded from the viewpoint of increasing safety in treatment.

Accordingly, it is an object of the present invention to provide an ion beam delivery equipment and an ion beam delivery method, which are able to confirm whether the SOBP width is a specified value during irradiation of ion beam.

To achieve the above object, the ion beam delivery equipment of the present invention is featured in comprising a first dose monitor installed upstream of a range modulation wheel (RMW) being rotated, the RMW having a thickness varied in the direction of travel of the ion beam to change energy of the ion beam passing the RMW, thereby forming a spread-out Bragg peak width in an irradiation target; a second dose monitor installed downstream of the RMW in the direction of travel of the ion beam; and a spread-out Bragg peak width computing unit for computing the spread-out Bragg peak width based on a first value (ionization charge) counted by the first dose monitor and a second value (ionization charge) counted by the second dose monitor.

With the present invention, since the spread-out Bragg peak width is computed based on the first value (ionization charge) counted by the first dose monitor and the second value (ionization charge) counted by the second dose monitor, whether the spread-out Bragg peak width formed in the irradiation target is a desired width can be confirmed during the irradiation of the ion beam.

Preferably, the computation of the spread-out Bragg peak width based on the first value and the second value is performed by using a ratio of the detected first value to the detected second value. Computing the spread-out Bragg peak width by using such a ratio enables the spread-out Bragg peak width to be determined with a high accuracy.

Preferably, the ion beam delivery equipment includes a spread-out Bragg peak width measuring unit for determining whether the computed spread-out Bragg peak width is equal to a specified width. With this feature, whether the spread-out Bragg peak width formed in the irradiation target is equal or nearly equal to the preset width can be easily confirmed in accordance with the result of the measurements.

Preferably, when the computed spread-out Bragg peak width is not equal or not nearly equal to the specified width, extraction of the ion beam from a beam generator is stopped. This feature contributes to improving safety in treatment using the ion beam directed to the irradiation target.

Thus, according to the present invention, whether the spread-out Bragg peak width is the specified value can be confirmed during the irradiation of the ion beam.

BRIEF DESCRIPTION OF THE DRAWINGS

FIG. 16 is a table for explaining one example of treatment plan information stored in a memory of an irradiation controller shown in FIG. 2;

FIG. 18 is an overall block diagram of ion beam delivery equipment according to a second embodiment of the present invention.

DESCRIPTION OF THE PREFERRED EMBODIMENTS

Embodiments of the present invention will be described in detail below with reference to the drawings.

First Embodiment

Figure 1:
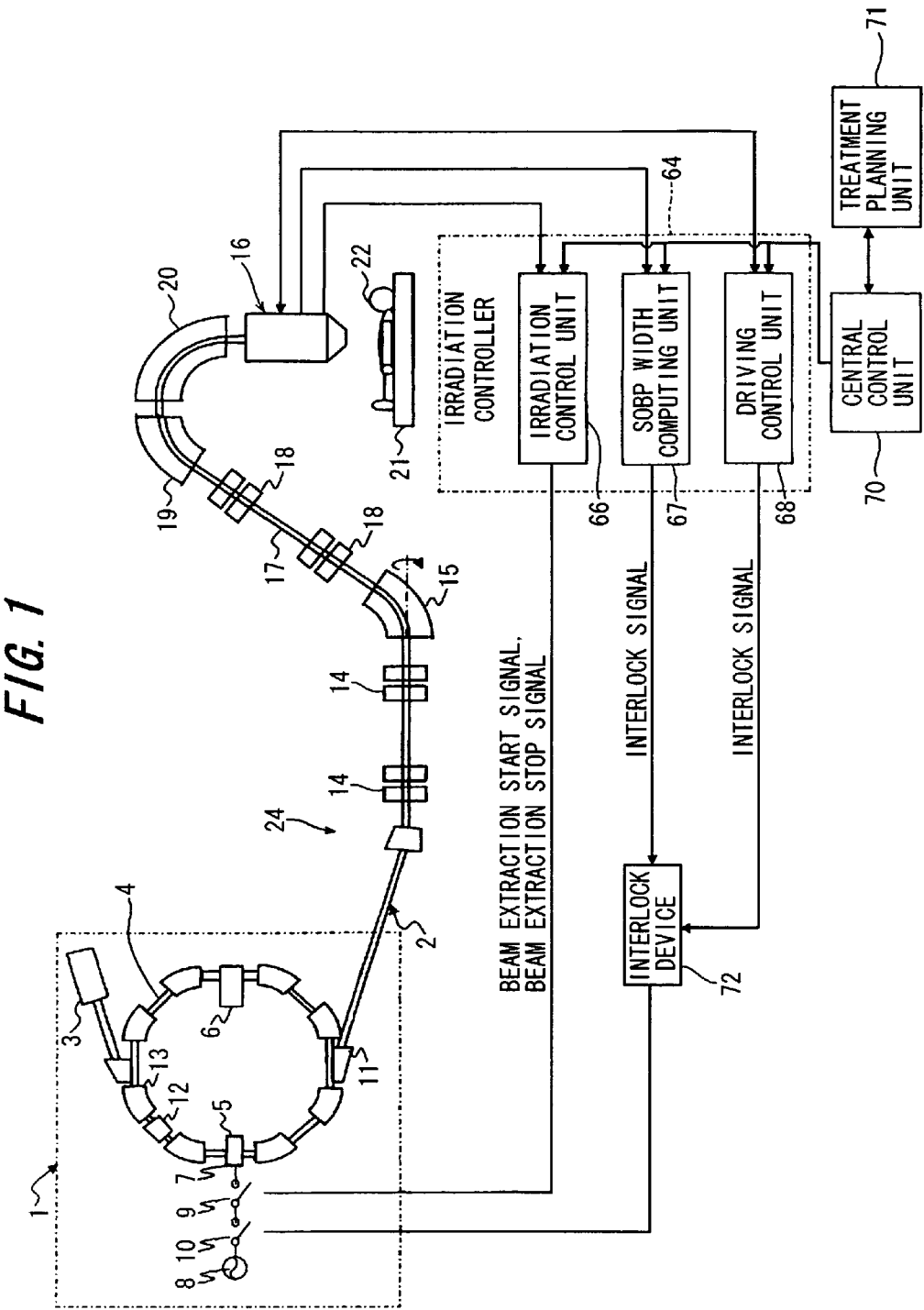
FIG. 1 is an overall block diagram of ion beam delivery equipment according to a first embodiment of the present invention.

An ion beam delivery equipment 24 as one preferred embodiment of the present invention will be described with reference to FIG. 1. The ion beam delivery equipment 24 of this embodiment comprises a beam generator 1, a beam transport system 2 connected to the beam generator 1 on the downstream side thereof, and a beam delivery nozzle 16 shaping the therapeutic radiation field. To be more specific, the ion beam delivery equipment 24 of this embodiment is a proton beam delivery equipment.

The beam generator 1 comprises an ion (proton) source (not shown), a pre-accelerator (e.g., a linear accelerator) 3, and a synchrotron 4 serving as a main accelerator. The synchrotron 4 includes an RF-applying device 5 and an RF-accelerating cavity (accelerating unit) 6. The RF-applying device 5 has a pair of electrodes 7, ON/OFF switches 9, 10 and a first RF-power supply 8. The electrodes 7 and the RF-accelerating cavity are installed on an orbit of a circulating ion beam. The first RF-power supply 8 is connected to the electrodes 7 through on/off switches 9, 10. A second RF-power supply (not shown) for applying an RF power to the RF-accelerating cavity 6 is separately provided. Ions (e.g., proton ions (or carbon ions)) generated by the ion source are accelerated by the pre-accelerator 3. An ion beam extracted from the pre-accelerator 3 enters the synchrotron 4. The ion beam (corpuscular beam) is given energy and thus accelerated by an electromagnetic field generated in the RF-accelerating cavity 6 with application of the RF power supplied from the second RF-power supply. The ion beam circulating in the synchrotron 4 is extracted from the synchrotron 4 upon closing of the on/off switch 9 after energy of the ion beam has been increased up to a specified level (e.g., 100 to 200 MeV). More specifically, when the on/off switch 9 is closed, an RF wave is applied to the circulating ion beam from the RF-applying device 5 through the first RF-power supply 8 and the on/off switches 10, 9 in the closed state. With the application of the RF power, the ion beam circulating within a separatrix is forced to transit to the outside of the separatrix and to be extracted from the synchrotron 4 through a beam extraction deflector 11. At the time of extracting the ion beam, currents supplied to quadrupole magnets 12 and bending magnets 13 both installed in the synchrotron 4 are held at setting current values, and hence the separatrix is also held substantially constant. The extraction of the ion beam from the synchrotron 4 is stopped by opening the on/off switch 9 (or the on/off switch 10) to stop the application of the RF power to the RF-applying device 5.

The ion beam extracted from the synchrotron 4 is transported downstream by the beam transport system 2. The beam transport system 2 includes quadrupole magnets 18 and bending magnets 19, 20, and the beam path 17 connected to the beam delivery nozzle 16. The beam delivery nozzle 16 and the beam path 17 are both mounted on a rotating gantry (not shown) installed in a treatment room (not shown). The quadrupole magnets 18, the bending magnet 19, and the bending magnet 20 are installed along the beam path 17 in this order. The ion beam is transported along the beam path 17 to the beam delivery nozzle 16. A patient 22 lies on a treatment couch 21 properly inserted in a treatment cage (not shown) formed within the rotating gantry. The ion beam from the beam delivery nozzle 16 is delivered to a tumor K (see FIG. 2 described later), such as a cancer, in the body of the patient 22. The beam path 17 including the magnets, such as the quadrupole magnets 18, can also be regarded as a beam transport system.

The beam delivery nozzle 16 will be described below with reference to FIG. 2. The beam delivery nozzle 16 has a casing 25 mounted to the rotating gantry and connected to the beam path 17. Also, within the casing 25, the beam delivery nozzle 16 has a beam profile monitor 26, a dose monitor (first dose monitor) 27, an RMW (range modulation wheel) device 28 serving as a Bragg peak width forming device, a second scatterer device 29, a range adjustment device (e.g., a range shifter) 30, a dose monitor (second dose monitor) 31, a flatness monitor 32, a block collimator 33, a patient collimator 34, and a range compensator 35, which are installed to lie on a beam path (beam axis) M within the casing 25 in this order from the upstream side in the direction of travel of the ion beam.

The beam profile monitor 26 is a monitor for confirming whether the ion beam having entered the beam delivery nozzle 16 from the beam transport system 2 is positioned on the beam axis M. The dose monitor 27 is a monitor for detecting the ionization charge of the ion beam having entered the beam delivery nozzle 16. The principle of detecting the dose of the ion beam will be described with reference to FIG. 3. The dose monitor 27 has a plurality of (e.g., five) electrodes 27a to 27c, which are installed one above another in parallel and are each very thin with a thickness of about several microns. Those five electrodes comprise a signal electrode 27a positioned at a center in the direction of travel of the ion beam and connected to a dose monitor counter 37, two positive electrodes 27b positioned to sandwich the signal electrode 27a therebetween and supplied with a positive voltage, and two outermost ground electrode 27c positioned to sandwich the two positive electrodes 27b therebetween. When the ion beam passes those electrodes, energy of the ion beam generates ionization charge between the signal electrode 27a and the two positive electrodes 27b, 27b, and the ionization charges are taken out through the signal electrode 27a. An amount of the ionization charge taken out through the signal electrode 27a is proportional to the dose of the ion beam. Therefore, the dose of the ion beam can be detected by counting the amount of the ionization charge with the dose monitor counter 37. The beam profile monitor 26 and the dose monitor 27 are both installed on a support table 39 mounted to the casing 25.

Figure 4:
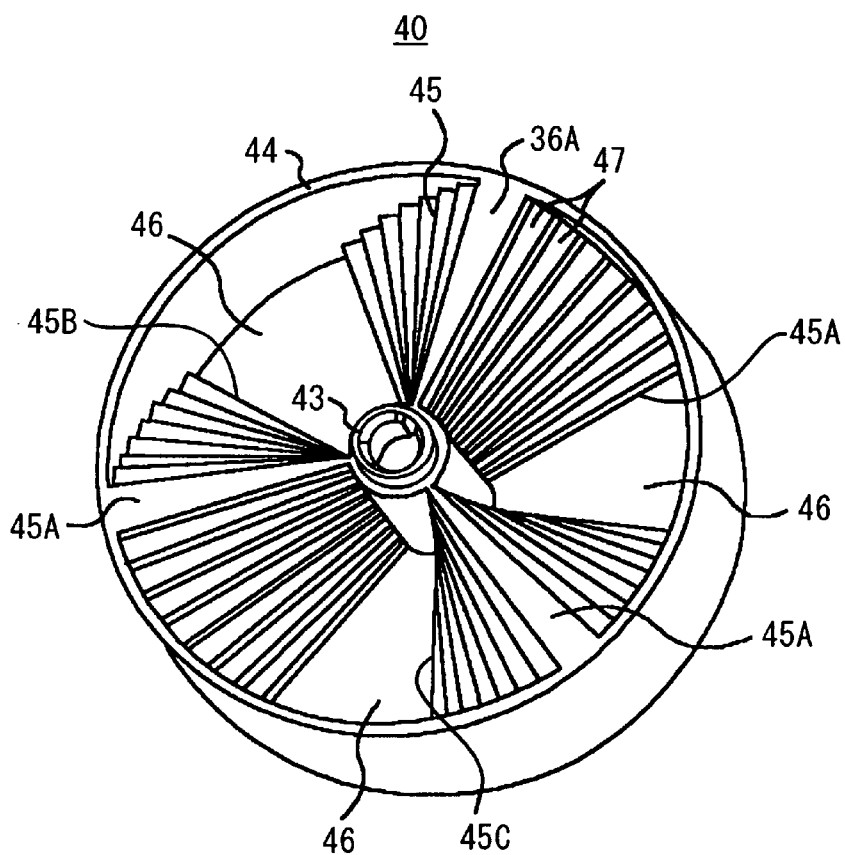
FIG. 4 is a perspective view of the RMW shown in FIG. 1.

Returning to FIG. 2, the RMW device 28 comprises an RMW 40, a rotation device (e.g., a motor) 42 for rotating the RMW 40, and an angle sensor 51 for detecting a rotational phase (angle) of the RMW 40. The RMW 40, the rotation device 42, and the angle sensor 51 are held by a support member 50 mounted to the casing 25. As shown in FIG. 4, the RMW 40 comprises a rotating shaft 43, a cylindrical member 44 installed in a concentric relation to the rotating shaft 43, and a plurality of blades 45 (three blades 45A, 45B and 45C in this embodiment) mounted to the rotating shaft 43. The blades 45 are extended in the radial direction of the RMW 40. An outer end of each of the blades 45 is mounted to the cylindrical member 44. Each of the blades 45 has a circumferential width larger at one end nearer to the cylindrical member 44 than at the other end nearer to the rotating shaft 43. An opening 46 is formed between adjacent two of the blades 45 in the circumferential direction (rotating direction) of the RMW 40. The opening 46 is also formed such that its circumferential width gradually increases toward an inner surface of the cylindrical member 44.

Each of the blades 45 has a plurality of plane areas (stepped portions) 47 arranged in the form of stairs in the circumferential direction of the RMW 40. Each of the plane areas 47 has a different thickness relative to a bottom surface of the RMW 40 in the axial direction of the rotating shaft 43 (i.e., the direction of the beam axis M). In other words, levels of the plane areas 47 relative to the bottom surface of the RMW 40 differ from one another. The thickness of each plane area 47 is called here the plane area thickness. More specifically, the plane area thickness of the blade 45 is increased in a stepwise way from each of the plane areas 47 adjacent to the openings 46, which are positioned on both sides of the blade 45 in the circumferential direction, toward the plane area 47 positioned at a top portion 36 having the largest thickness in the direction of the beam axis m. Each plane area 47 is extended from the rotating shaft 43 toward the cylindrical member 44 and has a circumferential width gradually increasing toward the cylindrical member 44.

The support member 50 mounted to the casing 25 has supports 50A, 50B opposing to each other in the direction of the beam axis M. The support member 50 also has a support 50C located downstream of the support 50B. The supports 50A, 50B rotatably support rotating shafts 48, 49, respectively. The RMW 40 is installed between the supports 50A and 50B. The rotating shaft 43 of the RMW 40 is supported by the rotating shafts 48, 49. More specifically, the rotating shaft 43 of the RMW 40 is detachably mounted to the rotating shafts 48, 49 so that the RMW 40 is replaceable. Respective ends of the rotating shafts 48, 49 are inserted in through holes 41 formed in the rotating shaft 43. The supports 50A, 50B are installed in positions not interfering with the beam path within the casing 25. The rotating shafts 43, 48 and 49 are also installed in positions away from the beam path.

The rotation device 42 mounted to the support 50C is coupled to the rotating shaft 49. The angle sensor 51 is coupled to the rotating shaft 48 and is mounted to the support 50A. A measured value of the rotational angle of the RMW 40 detected by the angle sensor 51 is inputted to an irradiation control unit 66 of an irradiation controller 64 described later.

Figure 2:
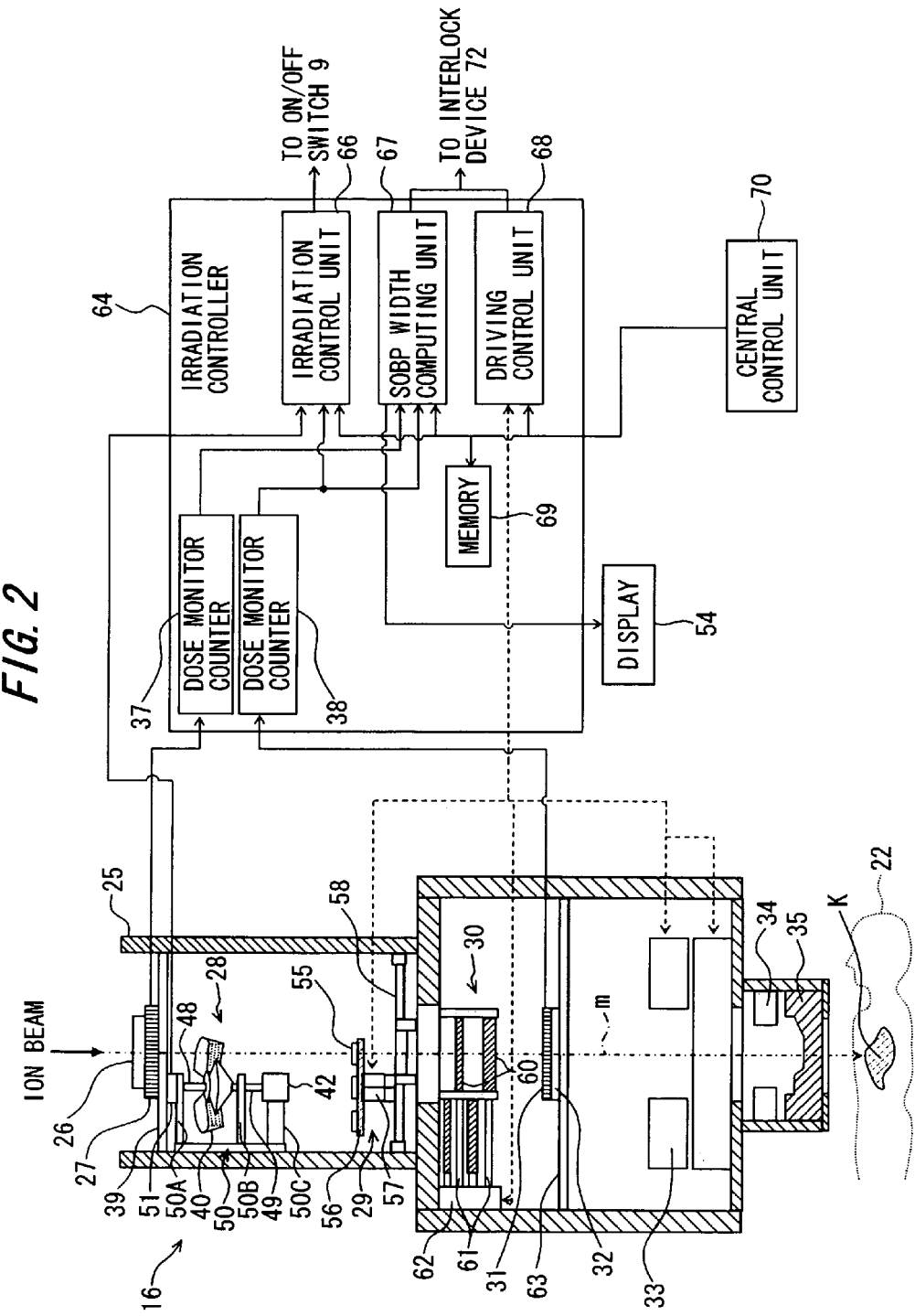
FIG. 2 is a vertical sectional view showing a detailed structure of an beam delivery nozzle shown in FIG. 1.

In this embodiment, though not shown in FIGS. 2 and 4, a first scatterer is further installed on the beam axis M between the RMW device 28 and the second scatterer device 29. The first scatterer is also mounted to the casing 25. The first scatterer has the function of spreading the ion beam having passed the RMW 40 in the direction perpendicular to the beam axis m.

The second scatterer device 29 comprises a plurality of second scatterers 55, a rotating table 56, and a motor 57. The motor 57 is installed on a support member 58 that is mounted to the casing 25. The plurality of second scatterers 55 for scattering the ion beam at degrees different from one another are arranged on the rotating table 56 side by side in the circumferential direction thereof. With the rotating table 56 rotated by the motor 57, predetermined one of the second scatterers 55 is positioned on the beam axis m. Driving of the motor 57 is controlled by a driving control unit 68.

The range adjustment device 30 comprises a plurality of absorbers 60 (four in this embodiment) differing in thickness from each other, and an absorber operating device 61 provided for each of the absorbers 60. The absorber operating device 61 is constituted as, e.g., an air cylinder driven by compressed air. Each absorber operating device 61 is driven by an absorber driver 62 that is controlled by the driving control unit 68.

The dose monitor 31 detects the ionization charge due to the ion beam having entered the beam delivery nozzle 16 and having passed the RMW device 28, the first scatterer, the second scatterer device 29, and the range adjustment device 30. The dose monitor 31 is of the same structure as the dose monitor 27. A dose monitor counter 38 counts the amount of ionization charge taken out through a signal electrode (not shown) of the dose monitor 31, thereby converted to the dose of the ion beam. Further, the flatness monitor 32 is a monitor for confirming flatness (dose uniformity) of the ion beam after being scattered by the first scatterer and the second scatterer device 55 in the direction perpendicular to the beam axis M. The dose monitor 31 and the flatness monitor 32 are installed on a support table 63.

The block collimator 33 shapes the ion beam in the planar direction perpendicular to the beam axis M, thereby roughly collimating the irradiation field of the ion beam. The aperture size of the block collimator 33 is variably controlled by the driving control unit 68. The patient collimator 34 finely collimates the ion beam in match with the shape of the tumor K in the body of the patient 22. The bolus 35 has the function of adjusting a penetration depth distribution of the ion beam match distal depth variation of the diseased part K (i.e., a tumor or a cancer) in the body of the patient 22 under treatment. Stated another way, the bolus 35 adjusts the penetrating range distribution of the ion beam to the shape of the tumor K as an irradiation target in the direction of depth.

Returning to FIG. 2, the ion beam delivery equipment 24 includes the irradiation controller 64. The irradiation controller 64 comprises the dose monitor counters 37, 38, an irradiation control unit (second controller) 66, a spread-out Bragg peak width computing unit (SOBP width computing unit) 67, the driving control unit 68, and a memory 69. The SOBP width computing unit 67 serves also as an SOBP width determining unit. The memory 69 stores irradiation condition information, described later, outputted from a central control unit 70. The irradiation control unit 66 performs extraction-on/off control of the ion beam from the beam generator 1 for forming the SOBP width. The SOBP width computing unit 67 computes the SOBP width of the ion beam being irradiated and determines whether the SOBP width is equal to the setting width. The driving control unit 68 controls respective operations of the motor 57 of the second scatterer device 29, the absorber driver 62 of the range adjustment device 30, and the block collimator 33. The ion beam delivery equipment 24 further comprises an interlock device (first controller) 72.

In the ion beam delivery equipment 24, a plurality of SOBP (Spread-out Bragg Peak) widths can be produced by making the extraction-on/off control of the ion beam from the beam generator 1 in accordance with the rotational angle of the RMW 40. The principle of that operation will be described below with reference to FIGS. 5, 6 and 7.

At the time when the ion beam passes the opening 46 of the RMW 40, the beam energy is not attenuated and therefore the Bragg peak is formed in a first deep position away from the body surface. At the time when the ion beam passes the plane area 47 of the blade 45 which is positioned at the top portion 36 and has the largest thickness, the beam energy is maximally attenuated and therefore the Bragg peak is formed in a shallow second position close to the body surface. At the time when the ion beam passes the plane area 47 positioned between the opening 46 and the top portion 36, the beam energy is attenuated at extent to the thickness of the blade at the position where the relevant plane area 47 is present, and therefore the Bragg peak is formed in a third position between the first position and the second position. Accordingly, when the ion beam is always in the beam-on state all over a 360°-region of the rotational angle in the circumferential direction of the RMW 40 as the case a shown in FIGS. 5 and 6, the Bragg peak cyclically varies between the first position and the second position with the rotation of the RMW 40. As a result, looking at the dose integrated over time, the case a) can provide a comparatively wide SOBP width ranging from a position near the body surface to a deep position as indicated by a relative dose distribution a) in the direction of depth, as shown in FIG. 7. The term "beam-on state" means a state in which the ion beam is extracted from the synchrotron 4 and emitted from the beam delivery nozzle 16 after passing the RMW 40. On the other hand, the term "beam-off state" means a state in which the ion beam is neither extracted from the synchrotron 4 nor emitted from the beam delivery nozzle 16.

Figure 5:
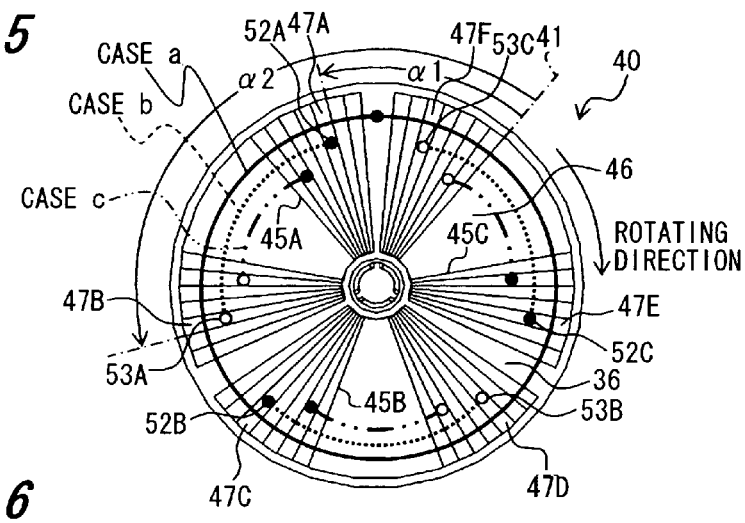
FIG. 5 is a plan view of the RMW shown in FIG. 4, the view showing, by way of example, ion beam delivery cases a to c.
Figure 6:
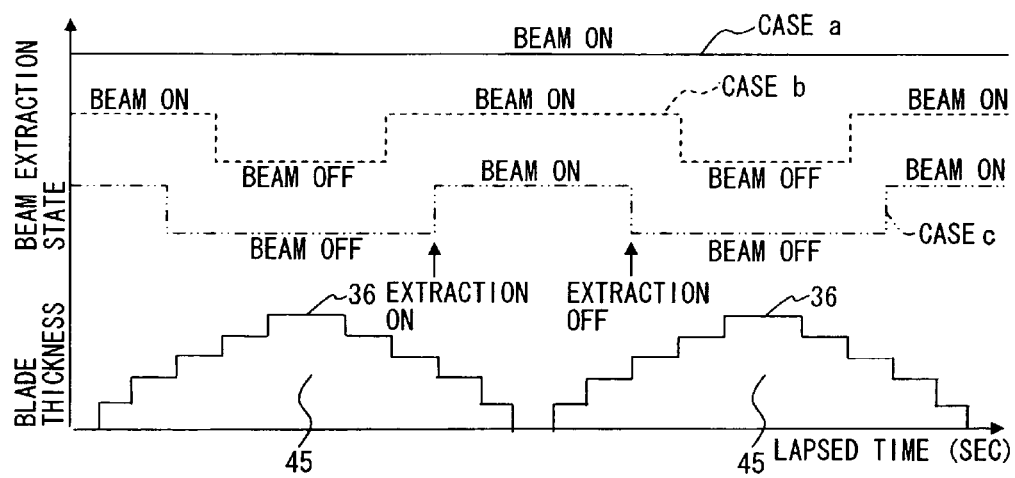
FIG. 6 is a chart showing beam-on and beam-off periods in each of the cases a to c, shown in FIG. 5, on the time serial base.
Figure 7:
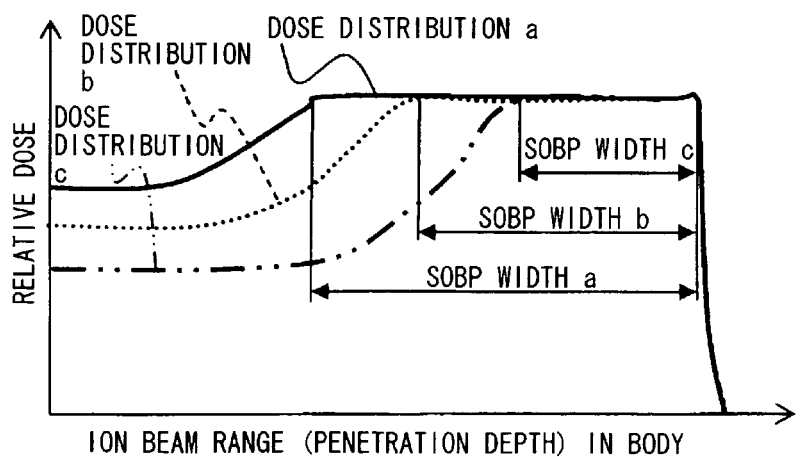
FIG. 7 is a graph showing a relative dose distribution and the SOBP width in the direction of depth in each of the cases a to c shown in FIG. 5.

In the case b) shown in FIGS. 5 and 6, the ion beam is brought into the beam-off state in a comparatively thick region (near the top portion 36) of each blade 45 in the circumferential direction of the RMW 40, while the ion beam is brought into the beam-on state in the other region of the rotational angle. Because no Bragg peak is formed in a shallow portion near the body surface, the case b) can provide an SOBP width indicated by a relative dose distribution b) in the direction of depth and having a narrower flat zone than the relative dose distribution a) as shown in FIG. 7.

In the case c) shown in FIGS. 5 and 6, the ion beam is brought into the beam-on state in the opening 46 and a comparatively thin region of each blade 45 near the opening 46 in the circumferential direction of the RMW 40, while the ion beam is brought into the beam-off state in the other region of the rotational angle. Because the attenuation rate of the beam energy is small as a whole, the Bragg peak is formed in a deep position away from the body surface in the case c). Therefore, the case c) can provide an SOBP width indicated by a relative dose distribution c) in the direction of depth and having a narrower flat zone than the relative dose distribution b) as shown in FIG. 7.

Thus, the ion beam delivery equipment 24 can form a plurality of different SOBP widths with one RMW 40 by making the extraction-on/off control of the ion beam in accordance with the rotational angle of the RMW 40 as described above.

The capability of forming various SOBP widths by the extraction-on/off control of the ion beam made during the rotation of the RMW 40 has much merit as described later. On the other hand, a capability of confirming whether the SOBP width desired for the patient is actually formed is one of important factors required for the ion beam delivery equipment from the viewpoint of increasing safety in the treatment using the ion beam while realizing that much merit. As a result of conducting intensive studies with intent to overcome such a problem, the inventors of this application have found that the SOBP width formed in the patient body can be confirmed even in the state of the ion beam being irradiated to the patient body based on the dose of the ion beam entering the RMW device 28 and the dose of the ion beam having passed the RMW device 28. Results of the studies conducted by the inventors will be described below.

The dose monitors 27, 31 each measure, as mentioned above, the amount of ionization charge generated upon incidence of the ion beam. The measured amount of the ionization charge is proportional to the energy of ions contained in the ion beam passing the relevant dose monitor and to the number of the ions. Therefore, respective count values of the amounts of the ionization charge obtained by the dose monitor counters 37, 38, which receive corresponding values of the amounts of ionization charge measured by and outputted from the dose monitors 27, 31, are each also proportional to the energy of the corresponding ions and the number of those ions.

The dose monitor 27 positioned on the most upstream side in the beam delivery nozzle 16 and is called here a reference monitor. The reference monitor 27 detects the ionization charge due to the ion beam entering the beam delivery nozzle 16 from the beam transport system 2. Because the energy of the ion beam entering the beam delivery nozzle 16 is constant, the energy of the ion beam passing the reference monitor 27 is constant. Accordingly, the count value of the measured ionization charge detected by the reference monitor 27 (hereinafter referred to as the "reference ionization charge value") is proportional to the number of the ions contained in the ion beam entering the reference monitor 27.

Figure 3:
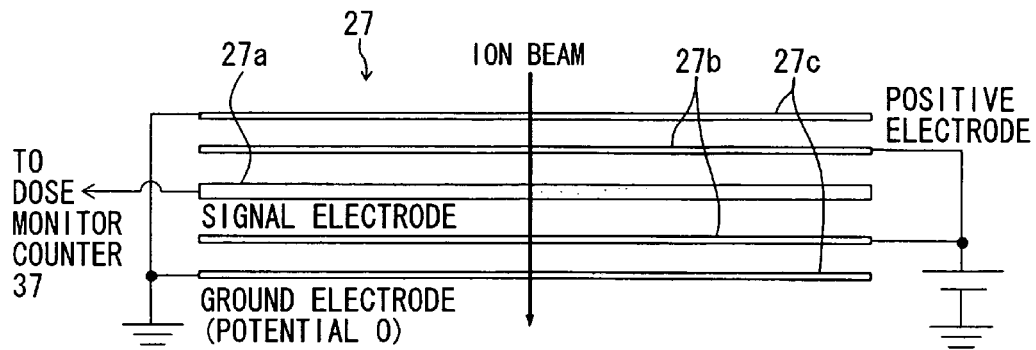
FIG. 3 is a schematic view showing a structure of a dose monitor shown in FIG. 1.
Figure 8:
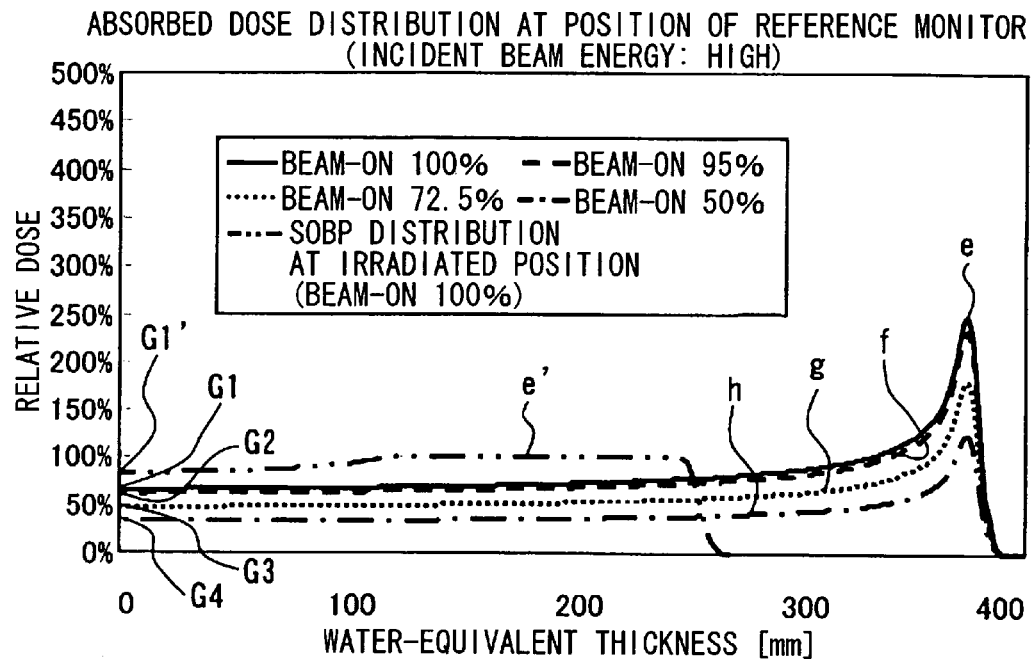
FIG. 8 is a graph showing relative dose distributions measured at the position of a reference dose monitor when an ion beam is irradiated while a percentage of the beam-on period is changed to four values.

The fact that the reference ionization charge value is proportional to the number of the ions is apparent from characteristics, shown in FIG. 8, measured by the inventors. Referring to FIG. 8, a curve e represents a relative dose distribution at the position of the reference monitor 27 resulting when a percentage of the beam-on period (angular range in which the ion beam is turned on) with respect to the overall 360°-circumference of the RMW 40 is 100%, and a curve f represents a relative dose distribution resulting when a percentage of the beam-on period is 95%. Also, a curve g represents a relative dose distribution resulting when a percentage of the beam-on period is 72.5%, and a curve h represents a relative dose distribution resulting when a percentage of the beam-on period is 50%. Because the reference monitor 27 has a very thin structure as shown in FIG. 3, the reference ionization charge value (i.e., the count value obtained by the dose monitor counter 27) depends on an absorbed ionization charge immediately after incidence into a substance. The term "absorbed ionization charge immediately after incidence into a substance" means an absorbed ionization charge at a water-equivalent thickness of 0 mm. Hence, the reference ionization charge values for the ion beams having the respective relative dose distributions e, f, g and h correspond to relative doses G1, G2, G3 and G4 (see FIG. 8). These relative doses G1, G2, G3 and G4 increase in proportion to the beam-on period (i.e., the number of the ions), as shown in FIG. 8. It is thus understood that the reference ionization charge value is proportional to the number of the ions in the ion beam entering the reference monitor 27.

The dose monitor 31 installed in the beam delivery nozzle 16 downstream of the range adjustment device 30 and upstream of the range compensator 35 is called here an main dose monitor 31. Because the main dose monitor 31 detects the dose of the ion beam at downstream of the RMW device 28, the energy of the ions passing the main dose monitor 31 is attenuated by the RMW 40 in a stepwise way. Accordingly, the count value of the measured ionization charge detected by the main dose monitor 31 (hereinafter referred to as the "main ionization charge value") is not simply proportional to the number of the ions, and it depends on how the energy of the ion beam is attenuated by the RMW 40 (i.e., the SOBP width).

Figure 9:
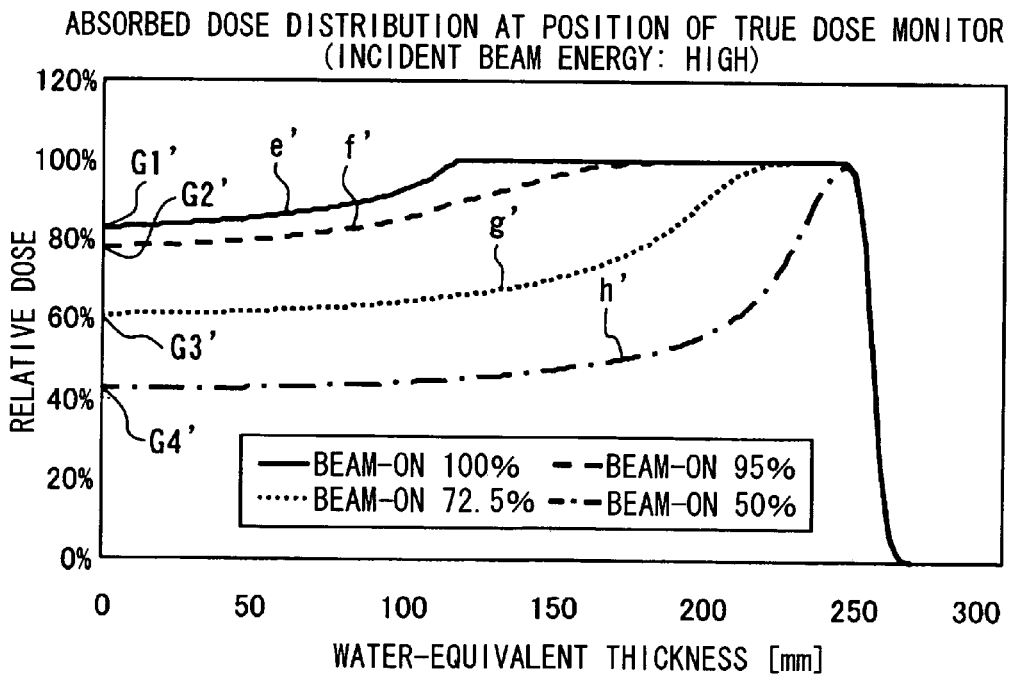
FIG. 9 is a graph showing relative dose distributions measured at the position of a main dose monitor when the ion beam is irradiated while a percentage of the beam-on period is changed to four values.

The fact that the main ionization charge value depends on the SOBP width is apparent from characteristics, shown in FIG. 9, measured by the inventors. Referring to FIG. 9, a curve e' represents a relative dose distribution at the position of the main dose monitor 31 resulting when a percentage of the beam-on period (angular range in which the ion beam is turned on) with respect to the overall 360°-circumference of the RMW 40 is 100%, and a curve f' represents a relative dose distribution resulting when a percentage of the beam-on period is 95%. Also, a curve g' represents a relative dose distribution resulting when a percentage of the beam-on period is 72.5%, and a curve h' represents a relative dose distribution resulting when a percentage of the beam-on period is 50%. Then, as described above with reference to FIGS. 5 to 7, various SOBP widths can be formed by performing the extraction-on/off control of the ion beam during the RMW rotation depending on the rotational angle of the RMW 40. Accordingly, as shown in FIG. 9, different SOBP widths are formed at the relative dose distributions e', f', g' and h' such that a longer beam-on period provides a larger SOBP width. Thus, the main ionization charge values (i.e., the count values obtained by the dose monitor counter 38) for the ion beams having the respective relative dose distributions e', f', g' and h' correspond to relative doses G1', G2', G3' and G4' shown in FIG. 9. These relative doses G1', G2', G3' and G4' increase depending on the SOBP width, as shown in FIG. 9, because a longer beam-on period provides a larger SOBP width. For comparison, a two-dot-chain line in FIG. 8 represents the relative dose distribution e' at the position of the main dose monitor 31 resulting when a percentage of the beam-on period is 100%, for example. As seen from FIG. 8, the relative dose G1' at the position of the main dose monitor 31 increases as compared with the relative dose G1 at the position of the reference monitor 27 under an influence of the SOBP width.

Figure 10:
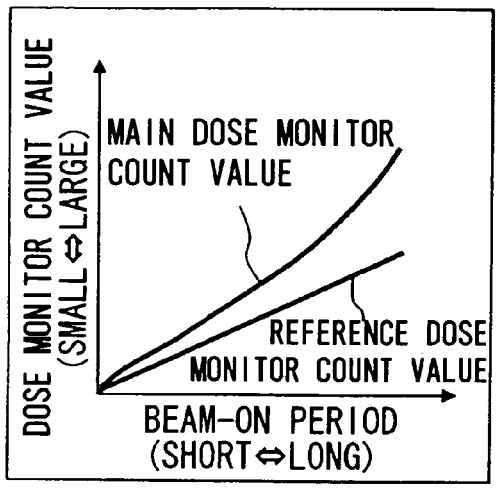
FIG. 10 is a characteristic graph showing changes of value (ionization charge) during the beam-on period counted by the main dose monitor and the reference dose monitor.

As shown in FIG. 10, the reference ionization charge value (the reference dose monitor count value) increases in proportion to the beam-on period. On the other hand, the main ionization charge value (the main dose monitor count value) increases at a higher rate than the reference ionization charge value as the beam-on period is prolonged, as shown in FIG. 10, because the main ionization charge value depends on both the beam-on period and the SOBP width. Thus, taking into account that the main ionization charge value depends on not only the SOBP width, but also the beam-on period (i.e., the number of the ions), the number of the ion in the ion beam must be averaged in order to specify the SOBP width on the basis of the main ionization charge value. Since the reference ionization charge value depends on only the number of the ions in the ion beam, the number of the ions can be averaged by dividing the main ionization charge value by the reference ionization charge value. In other words, a ratio resulting from dividing the main ionization charge value by the reference ionization charge value (hereinafter referred to as a main/reference ionization charge ratio) is a value depending on only the SOBP width.

Figure 11:
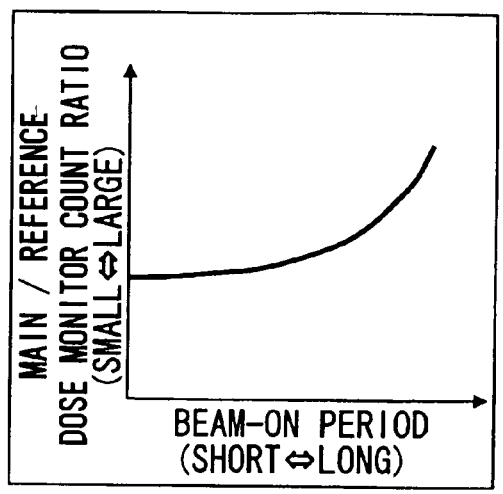
FIG. 11 is a characteristic graph showing changes of main/reference count (ionization charge) ratio during the beam-on period.
Figure 12:
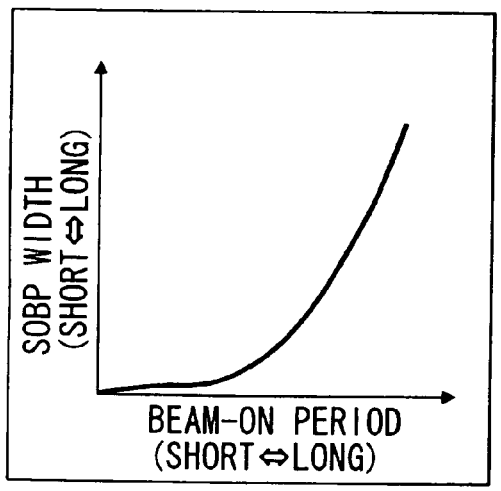
FIG. 12 is a characteristic graph showing changes of the SOBP width during the beam-on period.
Figure 13:
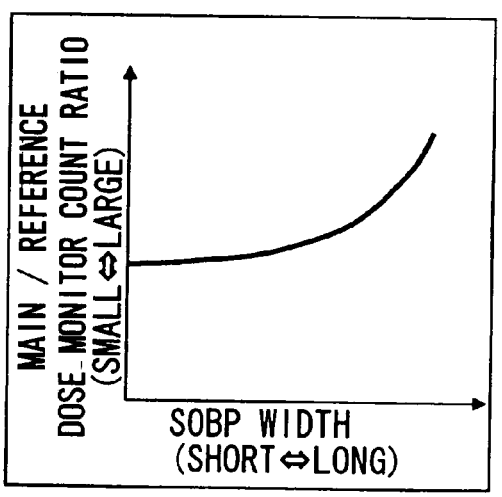
FIG. 13 is a characteristic graph showing changes of main/reference count (ionization charge) ratio with respect to the SOBP width.

FIG. 11 shows a characteristic curve representing the main/reference ionization charge ratio (the main/reference dose monitor count ratio) computed from the main ionization charge value and the reference ionization charge value shown in FIG. 10. Also, there is a relationship between the beam-on period and the SOBP width as shown in FIG. 12. Based on the characteristics shown in FIGS. 11 and 12, therefore, a characteristic curve representing the relationship between the main/reference ionization charge ratio (the main/reference dose monitor count ratio) and the SOBP width is derived as shown in FIG. 13. The relationship between the main/reference ionization charge ratio and the SOBP width represented by the characteristic of FIG. 13 is determined in advance through calculations, experiments, etc. Such a characteristic that the main/reference ionization charge ratio is related to the SOBP width is novel knowledge first found out by the inventors. Information of the characteristic representing the relationship between the main/reference ionization charge ratio and the SOBP width (e.g., information of the characteristic shown in FIG. 13) is stored in the memory 69 of the irradiation controller 64.

Figure 14:
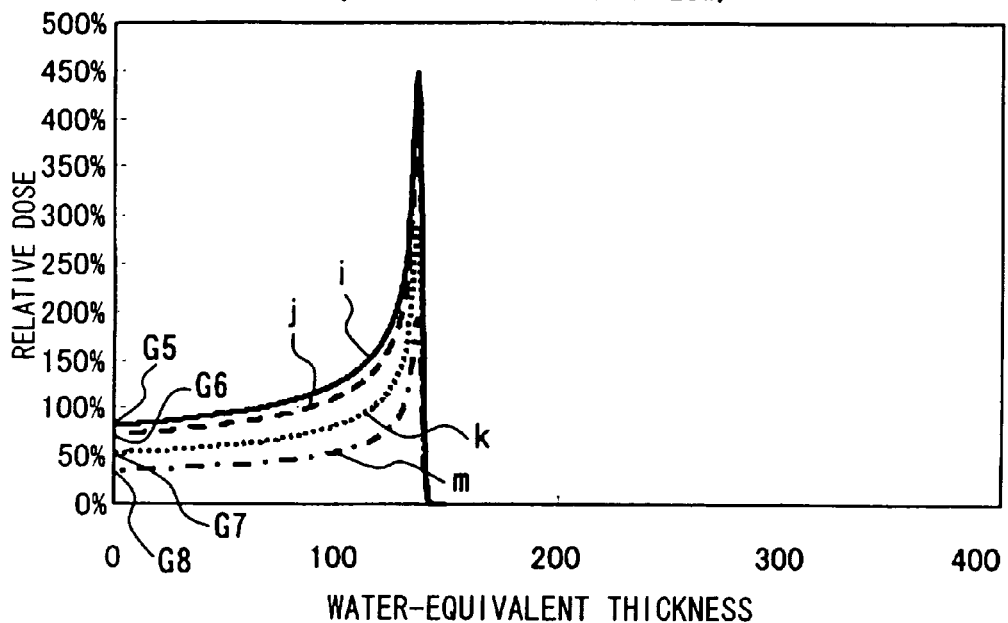
FIG. 14 is a graph showing relative dose distributions measured at the position of the reference dose monitor in the case of incident energy being set to be low when the ion beam is irradiated while a percentage of the beam-on period is changed to four values.
Figure 15:
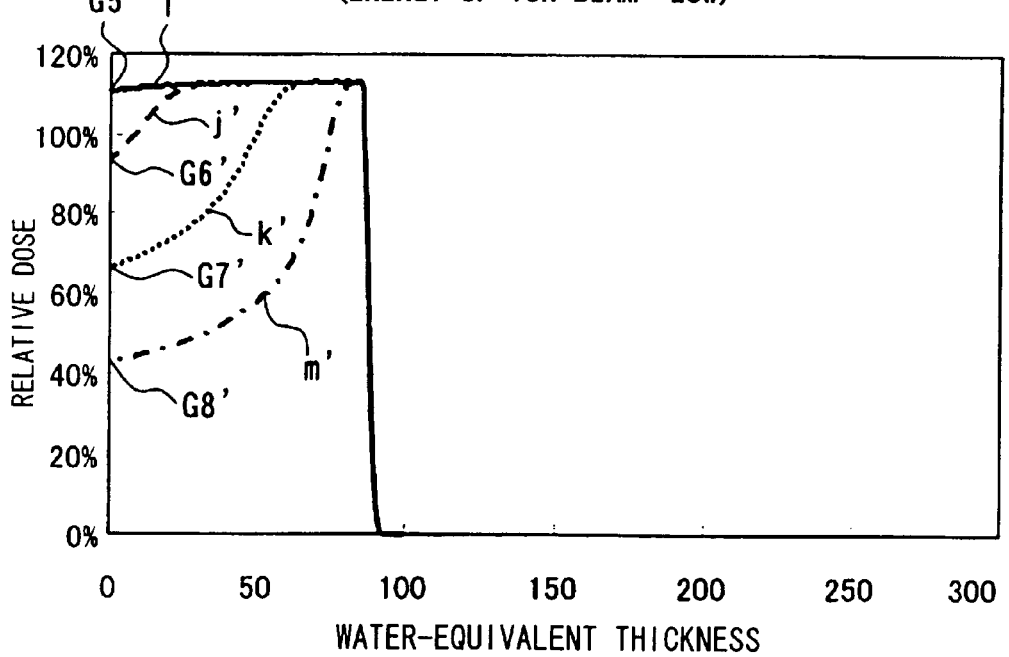
FIG. 15 is a graph showing relative dose distributions measured at the position of the main dose monitor in the case of incident energy being set to be low when the ion beam is irradiated while a percentage of the beam-on period is changed to four values.

The above description is premised on condition that the energy of the ion beam entering the beam delivery nozzle 16 is constant. If the energy of the beam changes, the characteristics representing the relative dose distributions at the positions of the reference monitor and the main dose monitor are also changed as shown in FIGS. 14 and 15, respectively. In the characteristics shown in FIGS. 14 and 15, the energy of the ion beam is set lower than that corresponding to the characteristics shown in FIGS. 8 and 9. Referring to FIG. 14, a curve i represents a relative dose distribution at the position of the reference monitor 27 resulting when a percentage of the beam-on period (angular range in which the ion beam is turned on) with respect to the overall 360°-circumference of the RMW 40 is 100%, and a curve j represents a relative dose distribution resulting when a percentage of the beam-on period is 95%. Also, a curve k represents a relative dose distribution resulting when a percentage of the beam-on period is 72.5%, and a curve m represents a relative dose distribution resulting when a percentage of the beam-on period is 50%. Referring to FIG. 15, a curve i' represents a relative dose distribution at the position of the main dose monitor 31 resulting when a percentage of the beam-on period (angular range in which the ion beam is turned on) with respect to the overall 360°-circumference of the RMW 40 is 100%, and a curve j' represents a relative dose distribution resulting when a percentage of the beam-on period is 95%. Also, a curve k' represents a relative dose distribution resulting when a percentage of the beam-on period is 72.5%, and a curve m' represents a relative dose distribution resulting when a percentage of the beam-on period is 50%. In the relative dose distributions i, j, k and m shown in FIG. 14, corresponding to the lower energy of the ion beam, the water-equivalent thickness is reduced and the relative dose is increased in comparison with the relative dose distributions e, f, g and h shown in FIG. 8. Likewise, in the relative dose distributions i', j', k' and m' shown in FIG. 15, corresponding to the lower energy of the ion beam, the water-equivalent thickness is reduced and the relative dose is increased in comparison with the relative dose distributions e', f', g' and h' shown in FIG. 9. Accordingly, relative doses G5, G6, G7 and G8 corresponding to the respective reference ionization charge values are increased in comparison with the above-mentioned relative doses G1, G2, G3 and G4. Also, relative doses G5', G6', G7' and G8' corresponding to the respective main ionization charge values are increased in comparison with the above-mentioned relative doses G1', G2', G3' and G4'. Further, as shown in FIG. 15, the formed SOBP width is narrowed in comparison with the SOBP width shown in FIG. 9. Hence, if the energy of the ion beam entering the beam delivery nozzle 16 changes, the characteristic showing the relationship between the main/reference ionization charge ratio (the main/reference dose monitor count ratio) and the SOBP width is also changed. In this embodiment, therefore, information of the characteristic representing the relationship between the main/reference ionization charge ratio (the main/reference dose monitor count ratio) and the SOBP width corresponding to each level of the energy of the ion beam is stored in the memory 69 of the irradiation controller 64.

Prior to starting the treatment using the ion beam delivery equipment 24, a physician makes a diagnosis based on a tomogram of the tumor K and thereabout in the body of the patient 22, which is taken by using an X-ray CT apparatus (not shown). Thereby, the physician confirms the position and size of the tumor K, and inputs information indicating the direction of irradiation of the ion beam, the maximum irradiation depth, etc. to a treatment planning unit 71. Based on the input information such as the direction of irradiation of the ion beam and the maximum irradiation depth, the treatment planning unit 71 computes the SOBP width, the irradiation field size, the target dose to be irradiated to the tumor K, etc. by using treatment planning software. Further, the treatment planning unit 71 computes various operation parameters (such as the energy of the ion beam extracted from the synchrotron 4, the angle of the rotating gantry, and the rotational angles of the RMW 40 when the extraction of the ion beam is turned on and off), and then selects the RMW 40 suitable for the treatment. Those various items of treatment plan information including not only the rotational angles and the target dose, but also the irradiation field size, the range, the energy of the ion beam (beam Eg), the thickness of the first scatterer (SC1 thickness), the SOBP width, the type of the second scatterer 55 (SC2 type), the thickness of the absorber 60 positioned in the beam path within the range adjustment device 30 (RS thickness), and the aperture size of the block collimator 33 (BC aperture size) which are listed in FIG. 16, are inputted to the central control unit 70 of the ion beam delivery equipment 24 and stored in a memory (not shown) of the central control unit 70. The above-stated treatment plan information is stored in the memory 69 of the irradiation controller 64 from the central control unit 70.

In accordance with the rotating gantry angle information inputted from the memory 69, a gantry controller (not shown) rotates the rotating gantry to direct the beam path within the beam delivery nozzle 16 toward the patient 22. Then, the treatment couch 21 on which the patient is lying is moved and positioned so that the tumor K lies on an extension of the beam path within the beam delivery nozzle 16.

By using the information stored in the memory 69 and regarding the irradiation field size, the range and the energy of the ion beam, the driving control unit 68 of the irradiation controller 64 selects respective values of the thickness of the first scatterer, the SOBP width, the type of the second scatterer, the absorber thickness, and the aperture size of the block collimator from the irradiation condition information stored in the memory 69, which is shown, by way of example, in FIG. 16. In accordance with the information regarding the thickness of the first scatterer, the driving control unit 68 moves the first scatterer having the selected thickness to position on the beam axis M. Then, the driving control unit 68 drives the motor 57 to rotate the rotating table 56 such that the selected second scatterer 55 is positioned on the beam axis M. The driving control unit 68 actuates the absorber operating device 61 through the absorber driver 62 such that the selected absorber 60 is positioned on the beam axis M. In accordance with the information regarding the aperture size of the selected block collimator 33, the driving control unit 68 controls a not-shown driver to move blocks of the block collimator 33 for setting its aperture size to a predetermined value.

The various items of the treatment plan information are displayed on a display installed in a control room for the ion beam irradiation equipment 24. The RMW 40, the bolus 35, and the patient collimator 34, which are suitable for the patient 22 who is going to take the treatment, are installed in the casing 25 of the beam delivery nozzle 16, as shown in FIG. 2, by an operator.

Based on the selected energy of the ion beam, the SOBP width computing unit 67 of the irradiation controller 64 reads, from the memory 69, the information representing the relationship between the main/reference ionization charge ratio and the SOBP width corresponding to the selected energy. The irradiation control unit 66 of the irradiation controller 64 reads, from the memory 69, the information regarding the rotational angles (e.g., $\alpha 1$ to $\alpha 6$ described later) of the RMW 40 and the target dose for the patient 22 who is going to take the treatment.

A method for treating the tumor K by using the ion beam delivery equipment 24 will be described below. The synchrotron 4 is operated by repeating the steps of injecting the ion beam from the pre-accelerator 3, and then accelerating, extracting and decelerating the ion beam. When the ion beam is accelerated until reaching the extraction energy at a setting level, the acceleration of the ion beam is brought to an end and the ion beam comes into a state ready for extraction from the synchrotron 4 (i.e., an ion beam extractable state). Information indicating the end of acceleration of the ion beam is transmitted to the central control unit 70 from a magnet power supply controller that monitors states of the magnets, etc. of the synchrotron 4 by using sensors (not shown).

The extraction-on/off control of the ion beam for forming the SOBP width in the ion beam delivery equipment 24 will be described below with reference to FIGS. 1, 2, 5 and 17. The following description of the extraction-on/off control of the ion beam is made, by way of example, in connection with the case b shown in FIG. 5. In the example of the case b, black points 52A, 52B and 52C each represent the timing of the extraction-on (start of extraction) of the ion beam, and white points 53A, 53B and 53C each represent the timing of the extraction-off (stop of extraction) of the ion beam. When the irradiation control unit 66 executes the control for the case b, it receives the rotational angles $\alpha 1$ to $\alpha 6$ ($\alpha 3$ to $\alpha 6$ are not shown), i.e., the setting values of the rotational angles, from the memory 69 beforehand. The rotational angle $\alpha 1$ represents an angle from a reference line 41 to the point 52A, and the rotational angle $\alpha 2$ represents an angle from the reference line 41 to the point 53A. The rotational angle $\alpha 3$ represents an angle from the reference line 41 to the point 52B, and the rotational angle $\alpha 4$ represents an angle from the reference line 41 to the point 53B. The rotational angle $\alpha 5$ represents an angle from the reference line 41 to the point 52C, and the rotational angle $\alpha 6$ represents an angle from the reference line 41 to the point 53C. The rotational angles $\alpha 1$ to $\alpha \neq$ each represent an angle on the basis of the state in which the reference line 41 is positioned on the beam axis M. In FIG. 5, the position of each black point represents a position where the extraction of the ion beam is started, while the position of each white point represents a position where the extraction of the ion beam is stopped.

Figure 17:
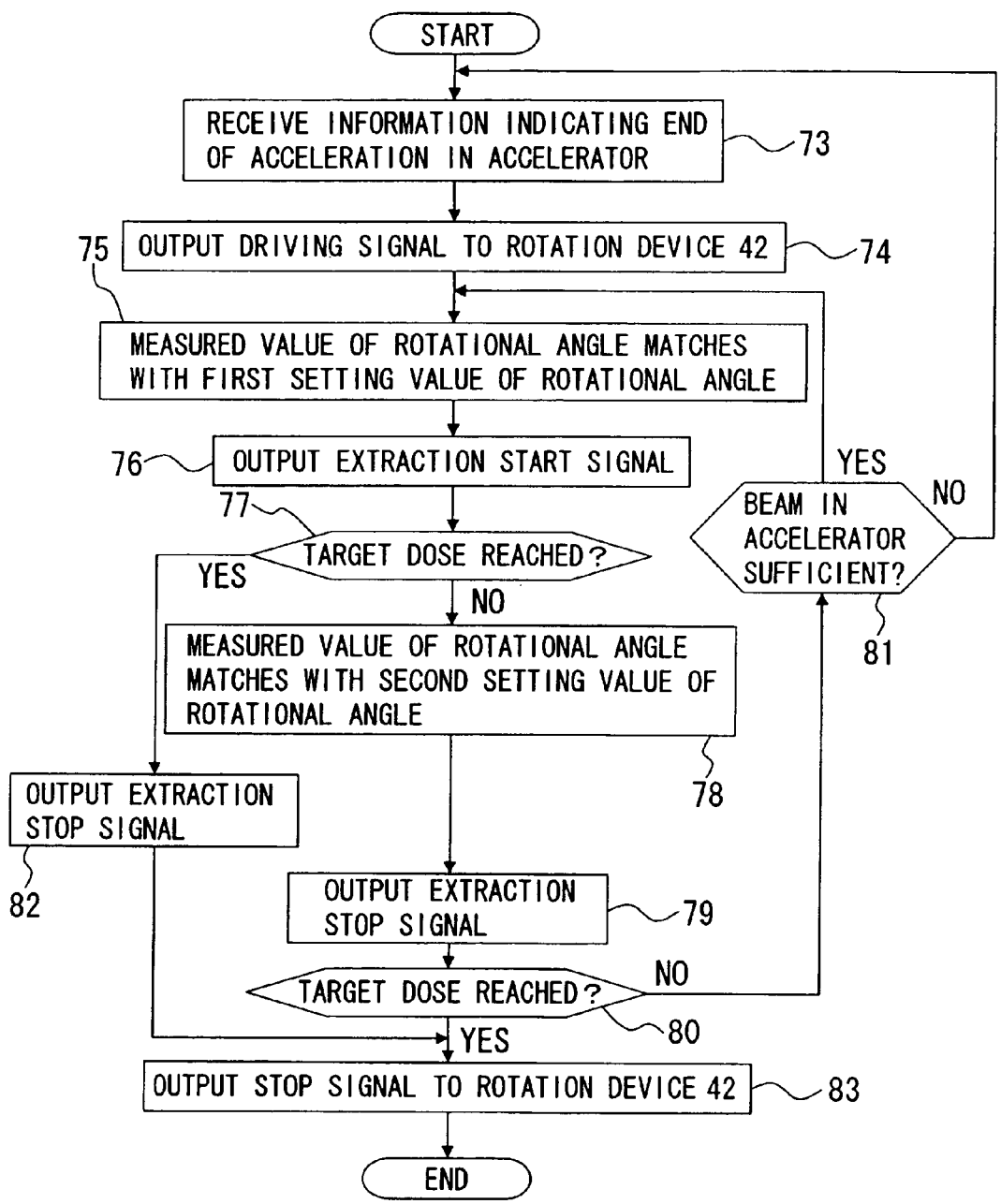
FIG. 17 is a flowchart showing control steps executed by an irradiation control unit shown in FIG. 1.

The irradiation control unit 66 executes the extraction-on/off control of the ion beam in accordance with a control flow shown in FIG. 17. First, the irradiation control unit 66 receives a signal indicating the end of acceleration in the accelerator (synchrotron 4) (i.e., a signal indicating that the ion beam is in the extractable state) (step 73). The end-of-acceleration signal is inputted from the central control unit 70. The irradiation control unit 66 outputs a start-of-rotation signal to the rotation device 42 (step 74). The rotation device 42 is rotated in accordance with the start-of-rotation signal. The torque of the rotation device 42 is transmitted to the rotating shaft 43 through the rotating shaft 49, whereby the RMW 40 is rotated. The number of rotations of the RMW 40 is set to a value in the range of 10 to 20 rotations per second. It is determined whether a measured value of the rotational angle matches with a first setting value of the rotational angle (step 75). More specifically, the measured value of the rotational angle of the RMW 40 measured by the angle sensor 39 is inputted to the irradiation control unit 66. It is then determined whether the input measured value matches with the first setting value of the rotational angle (any of the rotational angles $\alpha 1$, $\alpha 3$ and $\alpha 5$) at which a beam extraction start signal is to be outputted. If the measured value of the rotational angle matches with the first setting value, the beam extraction start signal is outputted (step 76). The on/off switch 9 is closed in response to the beam extraction start signal. The on/off switch 10 is held in the closed state. An RF power outputted is applied to the circulating ion beam from the RF-applying device 5 through the first RF-power supply 8, whereupon the ion beam is extracted from the synchrotron 4. The extracted ion beam is transported to the beam delivery nozzle 16.

The transported ion beam travels along the beam axis M within the beam delivery nozzle 16. The ion beam passes the beam profile monitor 26 and the reference monitor 27. The reference monitor 27 measures the dose (reference dose) of the ion beam. The measured reference ionization charge is inputted to the dose monitor counter 37. The ion beam having passed the rotating RMW 40 is spread out by the first scatterer in the direction perpendicular to the beam axis M. Then, the relative dose distribution of the ion beam is flattened by the second scatterer 55 in the direction perpendicular to the beam axis M. By subsequently passing the absorber 60 of the range adjusting device 30, the energy of the ion beam is reduced for adjustment of the range to be obtained in the body of the patient 22. The ionization charge due to the ion beam having passed the absorber 60 is measured by the main dose monitor 31, and the flatness of the ion beam in the direction perpendicular to the beam axis M is confirmed by the flatness monitor 32. The measured main ionization charge is inputted to the dose monitor counter 38. The ion beam further passes the block collimator 33, the patient collimator 34, and the bolus 35. Following that, the ion beam is emitted from the beam delivery nozzle 16 along the beam axis M and irradiated to the tumor K.

It is determined from the dose monitor count whether a dose delivered to the tumor K has reached the target value (step 77). Further, it is determined whether the measured value of the rotational angle matches with a second setting value of the rotational angle (step 78). The dose delivered to the tumor K, which is evaluated by the main dose monitor 31, and the measured value of the rotational angle are always inputted to the irradiation control unit 66. In step 77, it is determined whether a total of the measured ionization charge from the main dose monitor 31 has reached the target value. If this determination result is "YES", the processing of step 82 is executed in precedence to the processing of step 78 and a beam extraction stop signal is outputted. In response to the output of the beam extraction stop signal, the on/off switch 9 is opened to stop the supply of the RF power to the RF-applying device 5. Accordingly, the extraction of the ion beam from the synchrotron 4 is stopped and the irradiation of the ion beam toward the patient 22 lying on the treatment couch 21 is brought to an end. A stop-of-rotation signal is then outputted to the rotation device 42 (step 83). Thereby, the rotation device 42 stops its rotation and the rotation of the RMW 40 is also stopped.

If the determination result in step 77 is "NO", the processing of step 78 is executed. If it is determined in step 78 that the measured value of the rotational angle matches with the second setting value of the rotational angle (any of the rotational angles α2, α4 and α6) at which the beam extraction stop signal is to be outputted, the beam extraction stop signal is outputted (step 79). In response to the beam extraction stop signal, as mentioned above, the on/off switch 9 is opened and the extraction of the ion beam from the synchrotron 4 is stopped. The period from the output of the beam extraction start signal in step 76 to the output of the beam extraction stop signal in step 79 represents a period during which, for example, a region from the plane area 47A of the blade 45A to the plane area 47B of the blade 45B intersects the beam axis M along which the ion beam travels, i.e., an effective beam-on period. The time taken from the closing of the on/off switch 9 to the start of extraction of the ion beam from the synchrotron 4 is not longer than 1/1000 sec, and conversely the time taken from the opening of the on/off switch 9 to the stop of extraction of the ion beam is also not longer than 1/1000 sec.

In step 80, it is determined again whether the dose delivered to the tumor K, which is evaluated based on the measured signal from the main dose monitor 31, has reached the target dose. If this determination result is "NO", the processing of step 81 is executed. Stated another way, it is determined whether a sufficient amount of the ion beam exists in the synchrotron 4 after the end of the beam-on period. The amount of the ion beam (i.e., the current density of the ion beam) is monitored by the magnet power supply controller based on a value measured by a sensor (not shown) installed in the synchrotron 4. The measured value of the current density of the ion beam is inputted to the irradiation control unit 66 via the central control unit 70. The determination in step 81 is made using the measured value of the current density. If the determination result in step 81 is "YES", the processing of steps 75 to 80 is executed again. The period from the output of the beam extraction start signal in step 76 to the output of the beam extraction stop signal in step 79 in this repeated process represents a period during which, for example, a region from the plane area 47C of the blade 45B to the plane area 47D of the blade 45C intersects the beam axis M, i.e., an effective beam-on period. The period during which, for example, a region from the plane area 47E of the blade 45C to the plane area 47F of the blade 45A intersects the beam axis M in the next repeated process of steps 75 to 80 also represents an effective beam-on period. Between the two beam-on periods adjacent to each other, there is a beam-off period as shown in FIG. 6. If, during the repeated process of steps 75 to 80, it is determined in step 77 or 80 that a total of the measured ionization charge has reached the target dose, the processing of step 83 is executed and the irradiation of the ion beam toward the patient 22 is brought to an end.

If the determination result in step 81 is "NO", the processing subsequent to step 73 is executed again. More specifically, if the current density of the ion beam circulating within the synchrotron 4 lowers and the extraction of the ion beam is disabled, the ion beam in the synchrotron 4 is decelerated. The magnet power supply controller reduces the current values supplied to the magnets installed in the synchrotron 4, the beam transport system 2, etc. The current values supplied to those magnets are held in the state allowing the ion beam to enter. The ion beam is introduced to the synchrotron 4 from the pre-accelerator 3. Then, the ion beam is accelerated until reaching the extraction energy, as described above. After the end of acceleration of the ion beam, the processing subsequent to step 73 is executed by the irradiation control unit 66.

Because the determination in step 77 is made between steps 76 and 78, the extraction of the ion beam can be stopped when the total of the measured ionization charge has reached the target dose during the period in which the ion beam passes the rotating RMW 40. It is hence possible to prevent the ion beam from being excessively delivered to the tumor K. For example, if the determination result in step 77 is made "YES" when the opening 46 between the blade 45A and the blade 45B, shown in FIG. 5, is positioned on the beam axis M, the extraction of the ion beam can be stopped immediately. Therefore, the irradiation of the ion beam to the tumor K can be avoided during the period from the time at which the opening 46 is positioned on the beam axis M to the time at which the point 53A corresponding to the second setting value of the rotational angle is positioned on the beam axis M.

In the example of the case b) described above, the region from the point 52A to the point 53A, the region from the point 52B to the point 53B, and the region from the point 52C to the point 53C each represent an ion beam passage region in the RMW 40. The region from the point 53A to the point 52B, the region from the point 53B to the point 52C, and the region from the point 53C to the point 52A each represent a region in the RMW 40 where the ion beam does not pass (i.e., an ion beam non-passage region). While the above description is made, by way of example, in connection with the case b), various SOBP widths can be formed by changing, for one unit of the RWM 40, the first setting values of the rotational angle at each of which the beam extraction start signal is to be outputted and the second setting values of the rotational angle at each of which the beam extraction stop signal is to be outputted. While the ion beam passes the opening 46 in each of the "beam-on" periods shown in FIG. 6, the irradiation control unit 66 may execute control such that the ion beam passes the top portion 36 of the blade in each of the "beam-on" periods instead of passing the opening 46. In such a case, for example, the irradiation control unit 66 outputs the beam extraction start signal when the point 53C shown in FIG. 5 has reached the position of the beam axis M, and outputs the beam extraction stop signal when the point 52A shown in FIG. 5 has reached the position of the beam axis M.

With the above-described extraction-on/off control of the ion beam performed by the irradiation control unit 66, the desired SOBP width decided for the patient 22 according to the treatment plan can be formed at the tumor K.

While the ion beam is delivered from the beam delivery nozzle 16 to the tumor K, the driving control unit 68 inputs respective device status information of the second scatterer device 29, the range adjustment device 30, and the block collimator 33 in real time (or, e.g., at intervals of a certain period). The device status information is detected by sensors (not shown) installed on those devices. The driving control unit 68 reads the device status information from the memory 69 and determines whether the read information matches with corresponding one of the type of the second scatterer, the thickness of the absorber, and the aperture size of the block collimator. If there is a mismatch in any device status information, i.e., if the result of the above determination is "NO", the driving control unit 68 outputs an interlock signal to the interlock device 72. In response to the interlock signal, the interlock device 72 opens the on/off switch 10. Accordingly, even with the on/off switch 9 kept in the closed state, the supply of an RF power from the first RF-power supply 8 to the RF-applying device 5 is stopped, whereby the extraction of the ion beam from the synchrotron 4 is also stopped. If that determination result is "YES", the interlock device 72 does not open the on/off switch 10 and therefore the extraction of the ion beam from the synchrotron 4 is continued when the on/off switch 9 is closed.

The SOBP width computing unit 67 determines whether the SOBP width of the ion beam being irradiated is equal to the predetermined width. This process will be described in more detail below. The SOBP width computing unit 67 receives the dose of the ion beam upstream of the RMW device 28, which is detected by the (reference) dose monitor 27 and counted by the dose monitor counter 37, and the dose of the ion beam downstream of the RMW device 28, which is detected by the (main) dose monitor 31 and counted by the dose monitor counter 38. Speaking more exactly, the SOBP width computing unit 67 receives the amount of the ionization charge and converts it into the dose. While the ion beam is being irradiated to the tumor K, the reference dose obtained by the dose monitor counter 37 based on the detected signal from the reference monitor 27 and the main dose obtained by the dose monitor counter 38 based on the detected signal from the main dose monitor 31 are inputted to the SOBP width computing unit 67 of the irradiation controller 64 in real time (or, e.g., at intervals of a certain period). The SOBP width computing unit 67 computes a main/reference ionization charge ratio based on the inputted reference dose and main dose, and then computes the SOBP width for the computed main/reference ionization charge ratio by employing the information of characteristics that is stored in the memory 69 and represents the relationship between the main/reference ionization charge ratio and the SOBP. The SOBP width computing unit 67 determines whether the computed SOBP width matches with the SOBP width (i.e., the SOBP width setting value) that is the treatment plan information inputted from the central control unit 70. The computed SOBP width (actual SOBP width) means an SOBP width actually formed in the body of the patient 22. If the actual SOBP width does not match with the SOBP width setting value, the SOBP width computing unit 67 outputs an interlock signal (SOBP width abnormal signal) to the interlock device 72. In this case, the interlock device 72 outputs a switch-off signal to the on/off switch 10 for opening it. Accordingly, the supply of an RF power from the first RF-power supply 8 to the RF-applying device 5 is stopped, whereby the extraction of the ion beam from the synchrotron 4 is also stopped. If the actual SOBP width matches with the SOBP width setting value, the SOBP width computing unit 67 outputs an SOBP width normal signal to the interlock device 72, and therefore the interlock device 72 does not output the switch-off signal. This case is regarded as indicating that the desired SOBP width is formed in the body of the patient 22, and the irradiation of the ion beam toward the patient 22 is continued. The irradiation of the ion beam is performed, as described above, until the main dose obtained based on the detected signal from the main dose monitor 31 reaches the target dose. The SOBP width abnormal signal or the SOBP width normal signal outputted from the SOBP width computing unit 67 is displayed on a display 54. The SOBP width computing unit 67 serves also as an SOBP width determining unit. Incidentally, the SOBP width setting values differs depending on the patient 22 and, even for the same patient 22, it also differs depending on a size reduction of the tumor K resulting from the progress of treatment.

With the ion beam delivery equipment 24 of this embodiment, since the on/off control of the ion beam is performed with the RMW 40 being rotated, the region in the RMW 40 where the ion beam passes the RMW 40 can be varied in the rotating direction of the RMW 40. Accordingly, a plurality of SOBP widths having different values in the direction of depth from the body surface of the patient 22 can be formed by using one RMW 40, and one RMW 40 can be used for a plurality of patients. In other words, the number of patients treatable using one RMW 40 is increased. Also, since a plurality of SOBP widths can be formed by using one RMW 40, it is possible to reduce the number of RMWs to be prepared in a cancer treatment center equipped with the ion beam delivery equipment 24. Further, since a plurality of SOBP widths can be formed by using one RMW 40, it is possible to reduce the number of times at which the RMW installed in the beam delivery nozzle 16 is to be replaced. This is advantageous in cutting the time required for preparations of the treatment and in increasing the number of patients treated by the ion beam delivery equipment 24. Especially, in this embodiment, since the on/off control of the ion beam is performed in accordance with the rotational angle (specifically the measured values and the setting values of the rotational angle) of the RMW 40, each particular SOBP width can be formed at high accuracy. By changing the rotational angle of the RMW in on/off control of the ion beam, the SOBP widths having various values can be formed.

In the synchrotron 4, the number of accelerated ions is constant. Therefore, even when the beam-on period is shortened, the current density of the ion beam extracted from the synchrotron 4 during the beam-on period can be increased by increasing the RF power supplied from the first RF-power supply 8 to the electrodes 7. Hence, the dose rate for irradiation to the patient (i.e., the radiation dose irradiated to the patient per unit time and per unit volume) can be increased even in a short beam-on period. In other words, the irradiation time of the ion beam can be reduced for the patient 22 having the tumor K with a small thickness or a small volume by irradiating the ion beam having the increased current density. This reduction of the irradiation time contributes to reducing the burden imposed on the patient 22 and increasing the number of patients treated per year. Further, even in the case of shortening the beam-on period, all of the circulating ion beam can be essentially extracted from the synchrotron 4 by increasing the RF power applied for the extraction of the ion beam as mentioned above. As a result, the degree of radiation accumulated in the components, such as the synchrotron 4, can be reduced.

As an accelerator, a cyclotron may also be used, instead of the synchrotron, for introducing an ion beam extracted from the cyclotron to the beam delivery nozzle 16. However, the cyclotron does not include the decelerating step unlike the synchrotron, and performs steps of entering, accelerating and extracting the ion beam in succession. Accordingly, if the "beam-on" period is shortened, the number of ions extracted from the beam delivery nozzle 16 per unit time is reduced, while the rate of dose irradiated to the tumor K is not changed. This results in a reduction of the SOBP width and is hence equivalent to a reduction of the volume subjected to the irradiation. As a result, even when the "beam-on" period is shortened, the irradiation time of the ion beam is not changed for the patient 22 having the tumor K with a small thickness or a small volume. If the extraction of the ion beam is turned off during or after the step of accelerating the ion beam in the cyclotron, the amount of the ion beam discarded is increased and the degree of radiation accumulated in the components, such as the cyclotron, is increased.

With the ion beam delivery equipment 24 of this embodiment, whether the actual SOBP width formed through the beam-on/off control during the rotation of the RMW 40 is equal to the SOBP width setting value can be confirmed in real time during the irradiation of the ion beam. When the actual SOBP width is not equal to the SOBP width setting value, the extraction of the ion beam can be stopped. It is therefore possible to prevent an abnormal SOBP width, which differs from the SOBP width set in the treatment plan, in the body of the patient 22. Consequently, safety in the treatment using the ion beam can be significantly improved. In other words, according to this embodiment, the ion beam can be irradiated toward the patient 22 only when the SOBP width set in the treatment plan is formed in the body of the patient 22.

Because the SOBP width abnormal signal or the SOBP width normal signal outputted from the SOBP width computing unit 67 is displayed on the display 54, a physician (or a radiation engineer) is able to confirm whether the SOBP width formed in the body of the patient 22 is normal (or abnormal). Therefore, in the event that the extraction of the ion beam from the synchrotron 4 is not stopped with an abnormality occurred in the interlock device 72, etc. in spite of the SOBP width abnormal signal (SOBP width abnormal information) being displayed on the display 54, the physician (or the radiation engineer) is able to open the on/off switch 10 by depressing a beam extraction stop button installed on an operator condole (not shown) in the control room. The extraction of the ion beam from the synchrotron 4 can be hence manually stopped.

If the actual SOBP width does not match with the SOBP width setting value, this means that any abnormality occurs in any of the devices installed between the reference monitor 27 and the main dose monitor 31, i.e., the RMW device 28, the first scatterer, the second scatterer device 29, and the range adjustment device 30. In this embodiment, however, when there is no abnormality in the detected device status information (described above) regarding the first scatterer, the second scatterer device 29, and the range adjustment device 30, it can be specified that the abnormality is related to the RMW device 28 (namely, the desired SOBP width is not formed). As a modification, the main dose monitor 31 may be installed between the RMW device 28 and the second scatterer device 29 with the device status detected only for the RMW device 28.

The feature of confirming whether the actual SOBP width is normal (or abnormal) in this embodiment can be applied to not only the case of performing the beam-on/off control during the rotation of the RMW 40, but also the case of confirming the RMW having been replaced and installed for each patient in the beam delivery nozzle 16 in which the beam-on/off control is not performed during the rotation of the RMW 40. Usually, an identifier (e.g., a barcode) is attached to each RMW. Then, the beam delivery nozzle 16 is provided with a reader for reading the identifier, and the ion beam delivery equipment 24 has the interlock function of disabling the extraction of the ion beam when a false RMW is installed. Accordingly, in the event that the interlock function does not operate for some reason, application of the feature of confirming whether the actual SOBP width is normal (or abnormal) enables installation of a false RMW to be detected by confirming an abnormality of the actual SOBP width. As a result, safety of the ion beam delivery equipment can be further improved. Further, even in ion beam delivery equipment in which a ridge filter is used instead of the RMW to form the SOBP width, the extraction of the ion beam toward the patient can be avoided when a false ridge filter is installed, by applying the feature of confirming whether the actual SOBP width is normal (or abnormal).

Second Embodiment

Ion beam delivery equipment according to another embodiment of the present invention will be described below with reference to FIG. 18. Ion beam delivery equipment 24A of this second embodiment differs from the ion beam delivery equipment 24 of the above first embodiment in that the beam generator 1 including the synchrotron 4 is replaced with a beam generator 1A including a cyclotron 4A, and an energy changing device 86 is added to the beam transport system 2. The beam delivery nozzle 16 includes the RMW device 28.

The beam generator 1A comprises the cyclotron 4A having an accelerating device 85, an ion source 84, and the energy changing device 86. The energy changing device 86 is installed on the beam transport system 2 in a position near the cyclotron 4A. The energy changing device 86 comprises a plurality of plate-like degraders (not shown) allowing passage of the ion beam with an energy loss, a bending magnet (not shown) for bending the ion beam having reduced energy, an aperture (not shown) for cutting out a part of the ion beam after passing the bending magnet, and a beam shutter (not shown) for shutting out transport of the ion beam toward the downstream side of the beam transport system 2.

The on/off control of the ion beam by the irradiation control unit 66 is executed in accordance with steps 73 to 83 shown in FIG. 17. However, the extraction start signal outputted from the irradiation control unit 66 in step 76 is sent to an ion-source power supply device 87. The ion-source power supply device 87 supplies power to the ion source 84 upon input of the beam extraction start signal. The ion source 84 is thereby actuated to extract the ion beam. The extracted ion beam enters the cyclotron 4A and is accelerated by the accelerating device 81 until reaching a level of setting energy in the cyclotron 4A. The ion beam accelerated to the setting energy is extracted from the cyclotron 4A through an extraction deflector 11. Then, the beam extraction stop signal outputted in step 79 or 82 is sent to the ion-source power supply device 87, whereupon the ion-source power supply device 87 stops the supply of power to the ion source 84. Accordingly, entering of the ion beam to the cyclotron 4A is stopped and the extraction of the ion beam from the cyclotron 4A is also stopped.

Also, when the SOBP width computing unit 67 outputs the SOBP width abnormal signal during the extraction of the ion beam, the interlock device 72 outputs a power supply stop signal to the ion-source power supply device 87. Hence, the supply of power to the ion source 84 from the ion-source power supply device 87 is stopped and the extraction of the ion beam from the cyclotron 4A is also stopped.

This second embodiment can provide the same advantages as obtainable with the above first embodiment except for two advantages; namely (1) the irradiation time of the ion beam can be reduced for the patient 22 having the tumor K with a small thickness or a small volume by irradiating the ion beam having the increased current density, and (2) a degree of radiation accumulated in the components can be reduced.

Instead of actuating or stopping the ion source 84, the on/off control of the ion beam can also be performed by opening or closing the beam shutter of the energy changing device 86. As an alternative, entering of the ion beam to the beam delivery nozzle 16 may be on/off-controlled by varying the passage of the ion beam with control of power supply to the bending magnet 15.

What is claimed is:

1. An ion beam delivery equipment for delivering a ion beam to an irradiation target, the equipment comprising:
   a beam generator for generating said ion beam;
   a beam delivery nozzle including a beam energy adjustment device having a thickness varied in the direction of travel of said ion beam extracted from said beam generator to change energy of said ion beam passing said beam energy adjustment device, thereby forming a spread-out Bragg peak width in said irradiation target, said beam delivery nozzle delivering said ion beam having passed said beam energy adjustment device to said irradiation target;
   a first dose monitor installed upstream of said beam energy adjustment device in the direction of travel of said ion beam;
   a second dose monitor installed downstream of said beam energy adjustment device in the direction of travel of said ion beam; and
   a spread-out Bragg peak width computing unit for computing the spread-out Bragg peak width based on a first ionization charge detected by said first dose monitor and a second ionization charge detected by said second dose monitor.

2. The ion beam delivery equipment according to claim 1, wherein said spread-out Bragg peak width computing unit computes the spread-out Bragg peak width based on the first ionization charge and the second ionization charge by using a ratio of the first ionization charge to the second ionization charge.

3. The ion beam delivery equipment according to claim 1, wherein said beam energy adjustment device includes a wheel having a thickness varied in the rotating direction to change energy of said ion beam passing said wheel.

4. The ion beam delivery equipment according to claim 3, further comprising a controller for controlling start and stop of extraction of said ion beam from said beam generator during rotation of said wheel.

5. The ion beam delivery equipment according to claim 4, wherein said controller controls start and stop of extraction of said ion beam depending on a rotational angle of said wheel.

6. The ion beam delivery equipment according to claim 1, wherein said beam energy adjustment device is a ridge filter having a thickness varied in the direction of travel of said ion beam.

7. The ion beam delivery equipment according to claim 1, further comprising a display for displaying the spread-out Bragg peak width.

8. An ion beam delivery equipment for transporting an ion beam to an irradiation target, the equipment comprising:
   a beam generator for generating said ion beam;
   a beam delivery nozzle including a beam energy adjustment device having a thickness varied in the direction of travel of said ion beam extracted from said beam generator to change energy of said ion beam passing said beam energy adjustment device, thereby forming a spread-out Bragg peak width in said irradiation target, said beam delivery nozzle emitting said ion beam having passed said beam energy adjustment device to said irradiation target;
   a first dose monitor installed upstream of said beam energy adjustment device in the direction of travel of said ion beam;
   a second dose monitor installed downstream of said beam energy adjustment device in the direction of travel of said ion beam; and
   a spread-out Bragg peak width determining unit for computing the spread-out Bragg peak width based on a first ionization charge detected by said first dose monitor and a second ionization charge detected by said second dose monitor, and determining whether the computed spread-out Bragg peak width is equal to a setting width.

9. The ion beam delivery equipment according to claim 8, further comprising a first controller for, when the computed spread-out Bragg peak width is not equal to the setting width, controlling said beam generator to stop extraction of said ion beam.

10. The ion beam delivery equipment according to claim 8, further comprising a display for displaying the computed spread-out Bragg peak width.

11. The ion beam delivery equipment according to claim 8, wherein said spread-out Bragg peak width determining unit computes the spread-out Bragg peak width based on the first ionization charge and the second ionization charge by using a ratio of the first ionization charge to the second ionization charge.

12. The ion beam delivery equipment according to claim 8, wherein said beam energy adjustment device includes a wheel having a thickness varied in the rotating direction to change energy of said ion beam passing said wheel.

13. The ion beam delivery equipment according to claim 12, further comprising a second controller for controlling start and stop of extraction of said ion beam from said beam generator during rotation of said wheel.

14. The ion beam delivery equipment according to claim 13, wherein said second controller controls start and stop of extraction of said ion beam depending on a rotational angle of said wheel.

15. The ion beam delivery equipment according to claim 8, wherein said beam energy adjustment device is a ridge filter having a thickness varied in the direction of travel of said ion beam.

16. The ion beam delivery equipment according to claim 12, wherein said wheel has a plurality of blades each having a thickness varied in the rotating direction to change energy of said ion beam passing the blade.

17. The ion beam delivery equipment according to claim 1, wherein said beam generator includes one of a synchrotron or a cyclotron.

18. The ion beam delivery equipment according to claim 9, wherein said beam generator includes one of a synchrotron having an RF-applying device, and said first controller stops application of an RF power to said RF-applying device to stop extraction of said ion beam from said synchrotron when the computed spread-out Bragg peak width is not equal to the setting width.

19. The ion beam delivery equipment according to claim 18, wherein said beam energy adjustment device includes a wheel having a thickness varied in the rotating direction to change energy of said ion beam passing said wheel, and
   wherein the equipment further comprises a second controller for controlling start and stop of extraction of said ion beam from said synchrotron during rotation of said wheel,
   said second controller performing the start and stop control of extraction of said ion beam by controlling start and stop of supply of an RF power to said RF-applying device.

20. The ion beam delivery equipment according to claim 9, wherein said beam generator includes a cyclotron and an ion source for introducing said ion beam to said cyclotron, and said first controller stops supply of a power to said ion source to stop extraction of said ion beam from said cyclotron when the computed spread-out Bragg peak width is not equal to the setting width.

21. The ion beam delivery equipment according to claim 9, wherein said beam generator includes a cyclotron and an ion source for introducing said ion beam to said cyclotron, the equipment further comprises an energy changing device for changing energy of said ion beam extracted from said cyclotron, and said first controller closes a shutter provided in said energy changing device to stop transport of said ion beam to said beam delivery nozzle when the computed spread-out Bragg peak width is not equal to the setting width.

22. An ion beam delivery method for emitting a ion beam extracted from a beam generator through an beam delivery nozzle, which includes a beam energy adjustment device having a thickness varied in the direction of travel of said ion beam to change energy of said ion beam passing said beam energy adjustment device, thereby forming a spread-out Bragg peak width in an irradiation target, the method comprising the steps of:

detecting a first ionization charge of said ion beam upstream of said beam energy adjustment device and detecting a second ionization charge of said ion beam downstream of said beam energy adjustment device in the direction of travel of said ion beam; and computing the spread-out Bragg peak width based on the first ionization charge and the second ionization charge.

23. The ion beam delivery method according to claim 22, wherein said step of computing the spread-out Bragg peak width based on the first dose and the second dose is performed by using a ratio of the first ionization charge to the second ionization charge.

24. The ion beam delivery method according to claim 22, wherein extraction of said ion beam from said beam generator is started and stopped during rotation of a wheel included in said beam energy adjustment device and having a thickness varied in the rotating direction to change energy of said ion beam passing said wheel.

25. The ion beam delivery method according to claim 24, wherein the extraction of said ion beam is started and stopped depending on a rotational angle of said wheel.

26. An ion beam delivery method for emitting a ion beam extracted from a beam generator through an beam delivery nozzle, which includes a beam energy adjustment device having a thickness varied in the direction of travel of said ion beam to change energy of said ion beam passing said beam energy adjustment device, thereby forming a spread-out Bragg peak width in an irradiation target, the method comprising the steps of:

detecting a first ionization charge of said ion beam upstream of said beam energy adjustment device and detecting a second ionization charge of said ion beam downstream of said beam energy adjustment device in the direction of travel of said ion beam; and computing the spread-out Bragg peak width based on the first ionization charge and the second ionization charge, and determining whether the computed spread-out Bragg peak width is equal to a setting width.

27. The ion beam delivery method according to claim 26, wherein the extraction of said ion beam is stopped whether the computed spread-out Bragg peak width is not equal to the setting width.

28. The ion beam delivery method according to claim 26, wherein the computed spread-out Bragg peak width is displayed on a display.

29. The ion beam delivery method according to claim 26, wherein said step of computing the spread-out Bragg peak width based on the first ionization charge and the second ionization charge is performed by using a ratio of the first ionization charge to the second ionization charge.

30. The ion beam delivery method according to claim 26, wherein extraction of said ion beam from said beam generator is started and stopped during rotation of a wheel included in said beam energy adjustment device and having a thickness varied in the rotating direction to change energy of said ion beam passing said wheel.

31. The ion beam delivery method according to claim 30, wherein the extraction of said ion beam is started and stopped depending on a rotational angle of said wheel.

* * * * *